United States Patent [19]
Sugiura et al.

[11] Patent Number: 5,835,207
[45] Date of Patent: Nov. 10, 1998

[54] OPTICAL MEMBER INSPECTING APPARATUS

[75] Inventors: Masayuki Sugiura; Masato Hara; Toshihiro Nakayama; Atsushi Kida, all of Tokyo, Japan

[73] Assignee: Asahi Kogaku Kogyo Kabushiki Kaisha, Tokyo, Japan

[21] Appl. No.: 710,531

[22] Filed: Sep. 19, 1996

[30] Foreign Application Priority Data

Oct. 2, 1995 [JP] Japan ................................ 7-255066
Oct. 4, 1995 [JP] Japan ................................ 7-257953

[51] Int. Cl.$^6$ ............................ G01B 9/00; G01N 21/00
[52] U.S. Cl. ................................ 356/124; 356/239
[58] Field of Search ...................... 356/124–127, 356/237, 239

[56] References Cited

U.S. PATENT DOCUMENTS

| | | | |
|---|---|---|---|
| 5,216,481 | 6/1993 | Minato | 356/240 |
| 5,243,542 | 9/1993 | Noguchi | 356/374 |
| 5,257,092 | 10/1993 | Noguchi et al. | 356/124 |
| 5,335,059 | 8/1994 | Maruyama et al. | 356/125 |
| 5,351,119 | 9/1994 | Nakatsue | 356/124 |
| 5,432,606 | 7/1995 | Noguchi et al. | 356/360 |
| 5,448,355 | 9/1995 | Noguchi et al. | 356/354 |

*Primary Examiner*—Frank G. Font
*Assistant Examiner*—Amanda Merlino
*Attorney, Agent, or Firm*—Greenblum & Bernstein, P.L.C.

[57] ABSTRACT

An optical member inspecting apparatus comprises an illuminating unit for illuminating a target lens to be inspected and a photographing unit to detect the light transmitted through the target lens. The illumination unit has a circular diffuser plate on which a semi-circular light intercepting plate is attached. The diffuser plate can rotate about a rotation axis. The target lens is supported by an X-Y stage that moves the target lens in a plane perpendicular to the rotation axis. An image processing unit detects brightness distributions at different rotational positions of the light intercepting plate to calculate a brightness difference which represents a deviation of the optical axis of the target lens from the rotation axis. The image processing unit controls the X-Y stage based on the brightness difference so as to correct the deviation.

23 Claims, 24 Drawing Sheets

OPTICAL MEMBER INSPECTING APPARATUS

BACKGROUND OF THE INVENTION

The present invention relates to an optical member inspecting apparatus for detecting optical defects in optical members, such as lenses, and particularly concerns an apparatus for automatically aligning an optical member to be inspected (target optical member or target lens) to a predetermined position in the apparatus.

Optical members, for example lenses, are designed so that an incident light beam will converge or diverge in a predetermined manner. However, if the refracting power of the lens varies in an irregular manner due to anomalies in the lens or if the surface of the lens has deposits attached thereto or flaws therein, the incident light beam is not properly refracted or is shaded or diffused, and the desired performance will not be obtained. In particular, in the case of lenses that are made by injection molding, depressions caused by a separation of the resin material from the die surface, or flaw marks in the form of ripples caused by a contraction of the resin, or jetting, i.e., a turbulent flow of molten resin during the molding of plastics which results in some portions of the lens having a different density compared with other portions of the lens, tend to occur easily and such defects must be detected in an efficient manner.

In conventional inspecting apparatuses, the lens must be located at a predetermined inspection position, generally at a predetermined position on an optical axis of the inspecting optical system. In conventional inspecting apparatuses it is difficult to automatically locate the lens at the predetermined position.

SUMMARY OF THE INVENTION

It is therefore an object of the present invention to provide an improved optical member inspecting apparatus which can automatically locate a target optical member at a predetermined inspection position.

The optical member inspecting apparatus according to the present invention comprises a device for illuminating an optical system including an optical member to be inspected, the optical system having positive power, a device for intercepting a part of the light emitted from the illuminating device, the light intercepting means being located between the illuminating means and the optical system so that the focal point of the optical system coincides with the light intercepting device. The light transmitting portion and the light blacking portion of the light intercepting device comprises a straight boundary line. A device for detecting an image of the optical member, is located at an opposite side of the illuminating device with the optical system therebetween. A device for rotating the light intercepting device about a rotation axis that intersects with the straight boundary line, and a device for moving the optical member in directions perpendicular to the rotation axis are provided. Further, a device for determining a deviation of the optical member from a standard position with respect to the rotation axis based on the image detected by the detecting device and a device for centering the optical member on the rotation axis by controlling the moving device based on the deviations are also provided.

The optical member inspecting apparatus may further comprises a device for inspecting the optical member based on a composite image composed a plurality of images detected under the different rotation positions of the light intercepting device.

The centering device may control the moving device so that the optical axis or a center of an outline or a gravity point of the optical member coincides with the rotation axis.

DETAILED DESCRIPTION OF THE PREFERRED EMBODIMENTS

Figure 1:
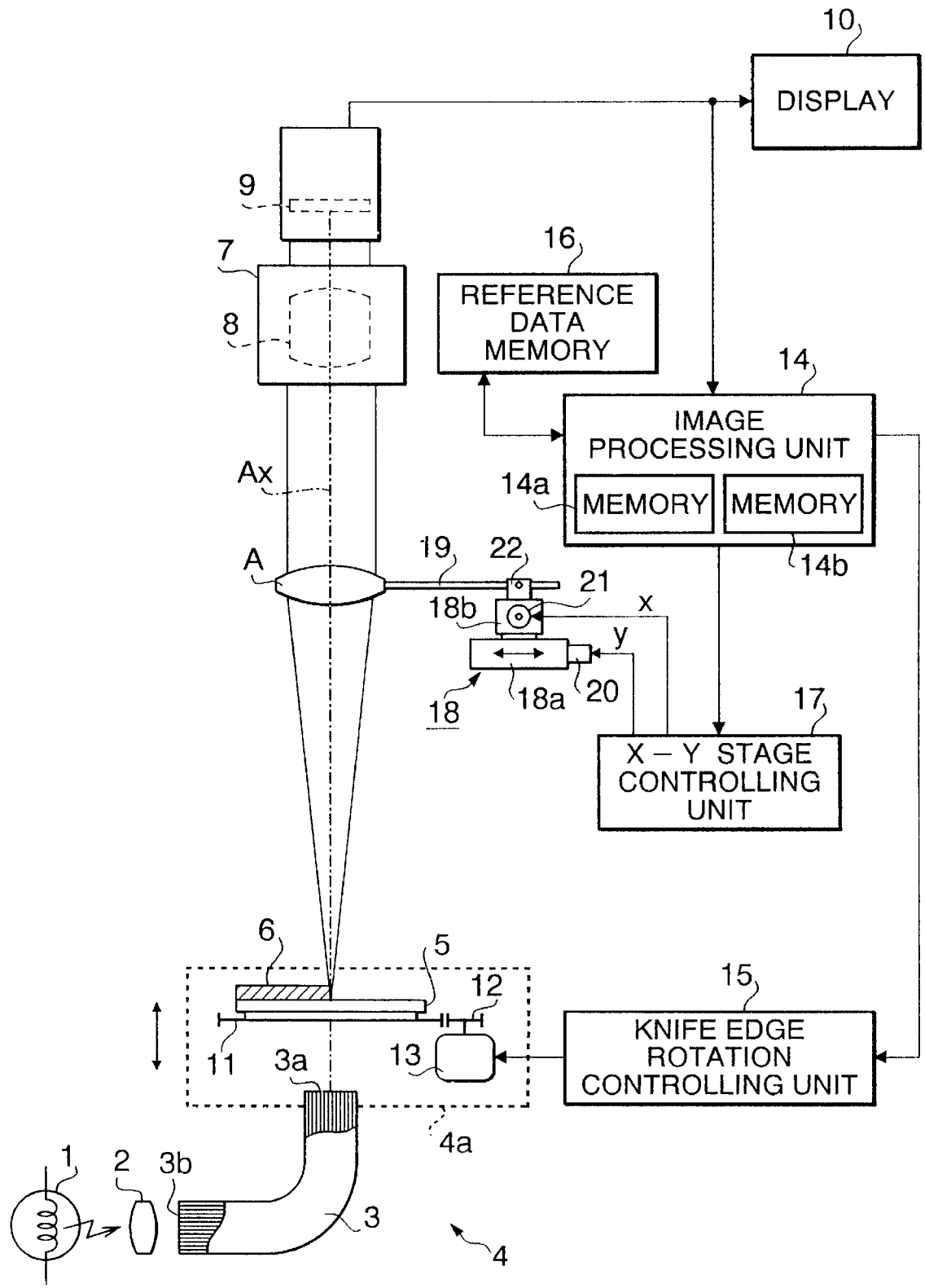
FIG. 1 shows a block diagram of the optical member inspecting apparatus of the first embodiment.
Figure 2:
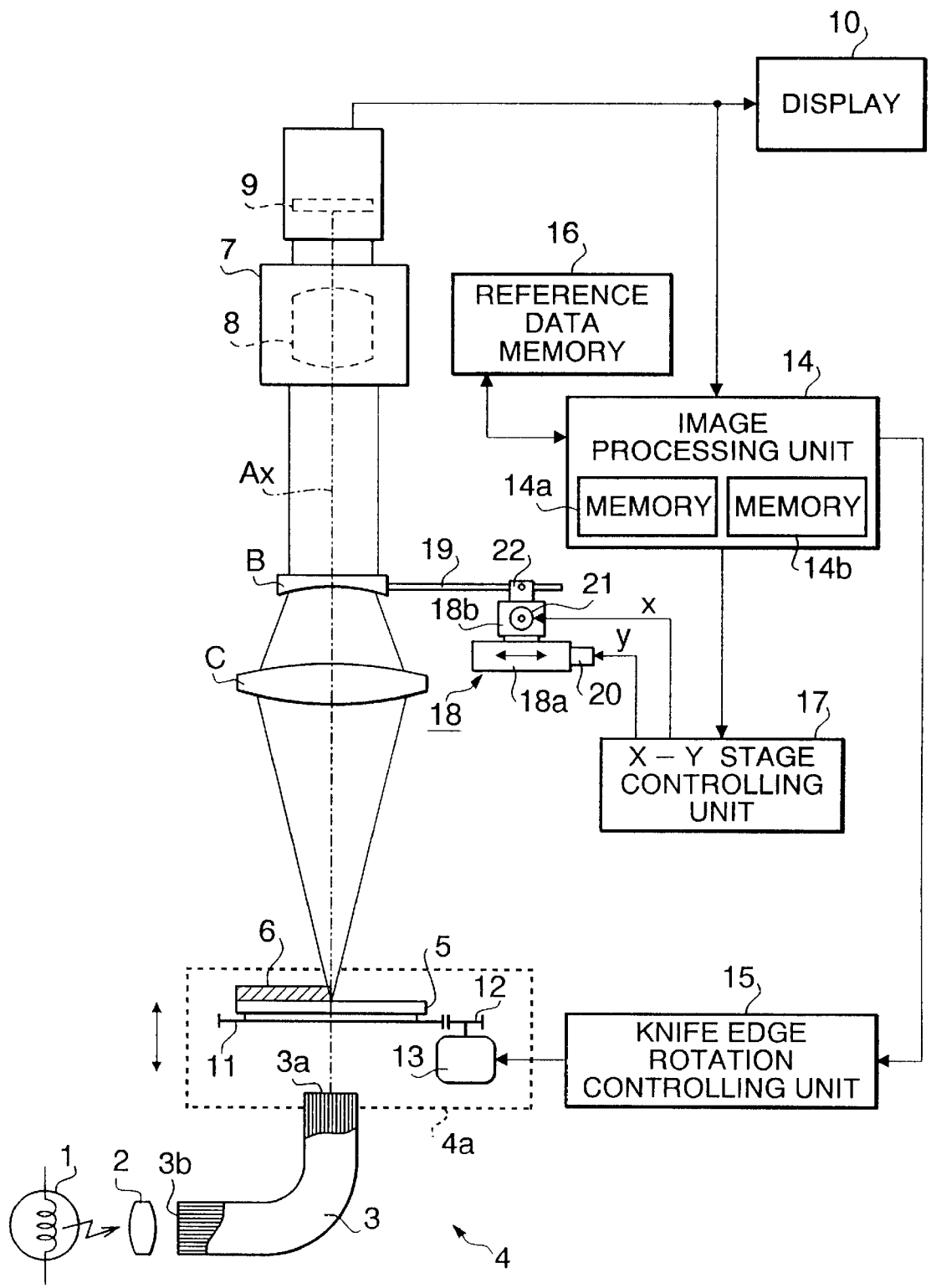
FIG. 2 shows a block diagram showing the case where the optical member inspecting apparatus of FIG. 1 is applied to a concave lens.

FIGS. 1 and 2 show block diagrams of the optical member inspecting apparatus. The elements shown are common to all three embodiments according to the invention described below.

As shown in FIGS. 1 and 2, an optical system of the optical member inspecting apparatus includes an illumination unit 4 and a photographing unit 7 which are coaxially arranged with a predetermined spacing. The illumination unit 4 is provided with a light source 1, a condenser lens 2, a light guide fiber bundle 3, and a diffuser unit 4a.

The diffuser unit 4a includes a circular diffuser plate 5 and a semi-circular light intercepting plate 6 attached to the diffuser plate 5.

Figure 3:
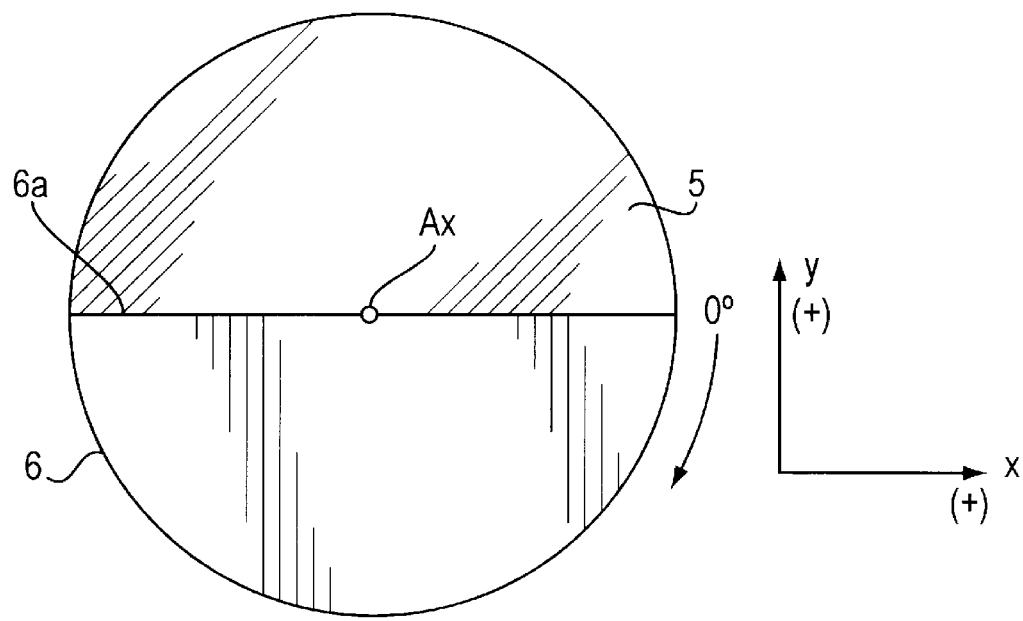
FIG. 3 is a view of a light intercepting plate shown in FIG. 1.

As shown in FIG. 3 that shows the diffuser plate 5 and the light intercepting plate 6 viewed from the photographing unit 7, the light intercepting plate 6 covers half of the diffuser plate 5 and straight edge (chord) of the light intercepting plate 6 defines a knife edge 6a that is a boundary line between an area through which a light beam transmits and an area in which the light beam is blocked.

The diffuser plate 5 can rotate about a rotation axis Ax with the light intercepting plate 6. The rotation axis Ax is normal to the surface of the diffuser plate 5 and at the center thereof. Since the knife edge 6a is formed as a diameter of the circular diffuser plate 5, the knife edge 6a intersects with the rotation axis Ax.

Figure 4:
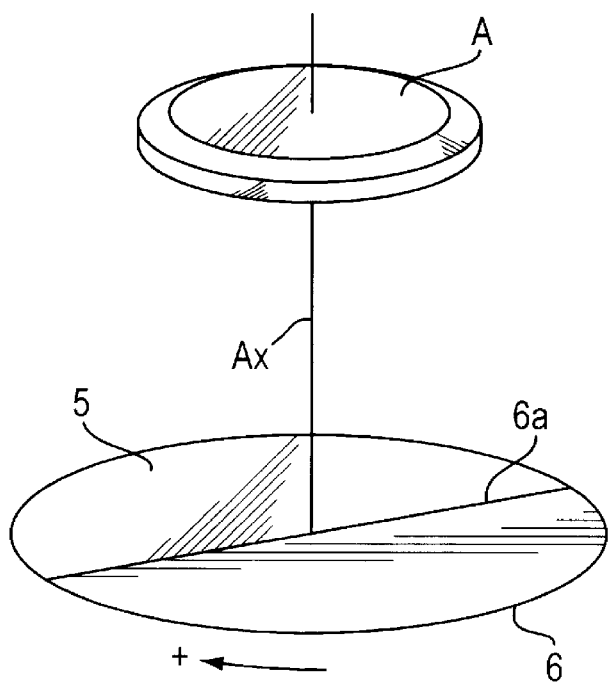
FIG. 4 is a perspective view which shows the rotating condition of the light intercepting plate.

FIG. 4 is a perspective view showing the diffuser plate 5 and the light intercepting plate 6 in relation to an optical member to be inspected (referred to as a target optical member A or a target lens A, but also includes a target lens system).

In a standard position, the light intercepting plate 6 covers the lower half of the diffuser plate 5 in FIG. 3 (the left half in FIG. 1) and a rotation angle is defined as being 0 degrees. The rotation angles of 90, 180, and 270 degrees are determined from the standard position in a clockwise direction as shown by an arrow. In FIG. 3, an x axis is defined by the knife edge 6a when the rotation angle equals 0 degrees or 180 degrees, and a y axis is defined by the knife edge 6a when the rotation angle is equal to 90 degrees or 270 degrees. For each axis, the positive axis is that of a standard coordinate system, as indicated by a plus sign.

Returning to FIGS. 1 and 2, the light emitted from the light source 1 is condensed by the condenser lens 2 to be incident on the light guide fiber bundle 3 at an incident end 3b. The light is transmitted by the fiber bundle 3 and exits from an exit end 3a of the fiber bundle 3. The exit light is then diffused by the diffuser plate 5 and half of the exit light is blocked by the light intercepting plate 6. The remaining half of the light that is not blocked by the light intercepting plate 6 is transmitted through a target lens and is detected by the photographing unit 7.

The target lens or target lens system must have positive power so that the front focal point of the target lens can be located on the diffuser plate 5. For example, when a positive target lens A shown in FIG. 1 is inspected, only the target lens A is located between the illumination unit 4 and the photographing unit 7. On the other hand, if the target lens has negative power, for example, a negative target lens B shown in FIG. 2, a supplementary lens C is required to ensure that the total optical system has positive power. In this case, both the negative target lens B and the supplementary lens C are located between the illumination unit 4 and the photographing unit 7.

The photographing unit 7 is provided with a photographing lens 8, which constitutes a positive lens system as a whole, and an image detecting element 9, such as a CCD area sensor. It is preferable that the rotation axis Ax of the diffuser plate 5 be coaxial with the optical axis of the photographing lens 8.

The image detecting element 9 captures an image formed by the photographing lens 8. The image detecting element 9 and the target lens A or B are optically conjugate via the photographing lens 8. That is, the image of the target lens A or B is formed on the image detecting element 9. The image detecting element 9 is formed as a two-dimensional array of pixels. After an image is captured, the image data is output from the image detecting element 9 as analog brightness data, i.e. gray-scale data for each pixel.

The image data output from the image detecting element 9 is sent to both a display 10, such as a CRT, and an image processing unit 14. The image data is displayed on the display 10 as a monochrome picture pattern in which the tone at each point represents the brightness data of a corresponding pixel. The image processing unit 14 converts the analog brightness data from the photographing unit 7 into 8-bit digital brightness data.

The image processing unit 14 is provided with a first and a second frame memory 14a and 14b, and is further connected to a reference data memory 16.

The diffuser unit 4a of the illumination unit 4 further includes an annular turntable 11 that has a gear around its circumference and a knife edge rotating motor 13. The gear engages a pinion 12 of the knife edge rotating motor 13. The knife edge rotating motor 13 is driven by a knife edge rotation controlling unit 15.

The diffuser unit 4a is moveable along the rotation axis Ax in order to adjust for the power of the target lens A or B such that the focal point of the target lens A, or the lens system including the target lens B and the supplementary lens C, coincides with the diffuser plate 5. The optical fiber bundle 3 is flexible and sufficiently long to allow such movement and the optical fiber bundle 3 follows the movement of the diffuser unit 4a so that appropriate illumination will always be provided.

The optical member inspecting apparatus further includes an X-Y stage 18 to support and align the target lens A or B along a plane perpendicular to the rotation axis Ax. The X-Y stage 18 consists of a Y stage 18a driven by a Y-axis pulse motor 20 and an X stage 18b which is mounted on the Y stage 18a and is driven by an X-axis pulse motor 21. A runner 19 formed on the target lens A or B is supported by a holding member 22 mounted on the X-stage 18b. According to instructions from the image processing unit 14, an X-Y stage controller 17 drives the pulse motors 20 and 21. The pulse motors 20 and 21 drive the X and Y stages 18b and 18a at 10 micrometers per pulse.

Using the above construction, a target lens is positioned such that its optical axis coincides with the rotation axis Ax and defects in the target lens can be effectively detected by capturing a plurality of images (for different angles of the light intercepting plate 6) with the image detecting element 9.

As is described in more detail below, the optical member inspecting apparatuses of the first and second embodiments undergo an adjustment process to adjust the position of the diffuser unit 4a, a centering process to align the optical axis of the target lens with the rotation axis Ax, a calibration process to make a data table for use in the centering process, and an inspection process. The optical member inspecting apparatus of the third embodiment further undergoes an initializing process to define a coordinate system in an image field, while also undergoing the adjustment process, a centering process to align the center of the target lens with the rotation axis Ax, and the inspection process. Thus, the adjustment process and the inspection process are common to all of the embodiments.

For the first and second embodiments, in the adjustment process, the diffuser unit 4a is manually adjusted so that the focal point of the target lens coincides with the diffuser plate 5. Then, in the centering process, the image processing unit 14 controls the X-Y stage 18 so that the optical axis of the target lens A or B coincides with the rotation axis Ax. Finally, in the inspection process, the image processing unit 14 determines whether the target optical member is acceptable or unacceptable based on the image data from the imaging element 9. During the centering process, the target lens is adjusted based on the output image data from the image detecting element 9 and the data table created in the calibration process and stored in the reference data memory 16.

For the third embodiment, in the initializing process the rotation axis Ax and the x-y coordinate system are defined for a captured image field taken without a target lens. Then, in the adjustment process, the illumination unit 4 is manually adjusted in the same manner as for the first and second embodiments. Next, in the centering process, the image processing unit 14 controls the X-Y stage 18 so that the center of the target lens A or B coincides with the rotation axis Ax according to the image data from the image detecting element 9. Finally, in the inspection process, the image processing unit 14 determines whether the target optical member is acceptable or unacceptable.

In all embodiments, after the adjustment process, the light emitted from a point on the diffuser plate 5 should become parallel light if the target lens is acceptable. Thus, from the view point of the photographing unit 7 (i.e. through the target lens A or B), the knife edge 6a of the light intercepting plate 6 is equivalent to an object positioned at infinity.

During the centering process, the image processing unit 14 instructs the knife edge rotation controlling unit 15 to rotate the diffuser plate 5 at 90 degree or 180 degree intervals. During the inspection process, the image processing unit 14 instructs the knife edge rotation controlling unit 15 to rotate the diffuser plate 5 in 22.5 degree intervals.

During the inspection process, when the straight knife edge 6a is inserted in the optical path, anomalies in a direction parallel to the knife edge 6a will be detected satisfactorily, however, anomalies in a direction orthogonal to the knife edge 6a will not be detected very well. Thus, by rotating the knife edge 6a itself in the plane orthogonal to the rotation axis Ax, anomalies in all directions can be detected.

Each embodiment will be described in detail with reference to the image patterns captured by the image detecting element 9 and to flow charts.

First embodiment

In the first embodiment, a standard lens having no defects, which is a prototype of the target lens A or B, is set on the X-Y stage 18 for executing the adjustment process. The adjustment process begins when the light source 1 is turned on to illuminate the diffuser plate 5. As a result, the image captured by the image detecting element 9 is shown on the display 10. The user then adjusts the diffuser unit 4a along the rotation axis Ax while observing the displayed image.

In particular, the user observes that the light intensity distribution of the displayed image varies depending on the distance between the focal point of the optical member and the diffuser plate 5 along the rotation axis Ax.

For example, FIGS. 5a through 5e show actual captured image patterns when the diffuser unit 4 is moved along the rotation axis Ax, i.e., when the distance between the focal point of the standard lens and the diffuser plate 5 varies. In this case, the standard lens is a rectangular shaped biconvex lens made of a synthetic resin of which front and rear surfaces are spherical. Black-white tones represent the brightness of a portion. These images are taken when the light intercepting plate 6 is located at the standard position (i.e. when the rotation angle equals 0 degrees as shown in FIG. 3). In the captured images, the x-y axes are defined in the same manner as those for the diffuser plate 5. However, the positive x axis appears opposite to that for the diffuser plate 5 since the point of view is reversed (i.e. now viewed from the illumination unit 4 side).

In FIGS. 5a through 5e, an image 100 of the standard lens is formed as a real inverted image, as shown by a dotted line, and an image 200 of the light intercepting plate 6 is formed as a real inverted image by the light that does not,pass through the standard lens. The image 100 of the standard lens is formed in an in focus condition and the image 200 of the light intercepting plate 6 is formed in an out of focus condition in the background of the image 100. Also, the image 100 of the standard lens may include a shading image of the light intercepting plate 6, as formed by the light transmitted through the standard lens.

Figure 5A:
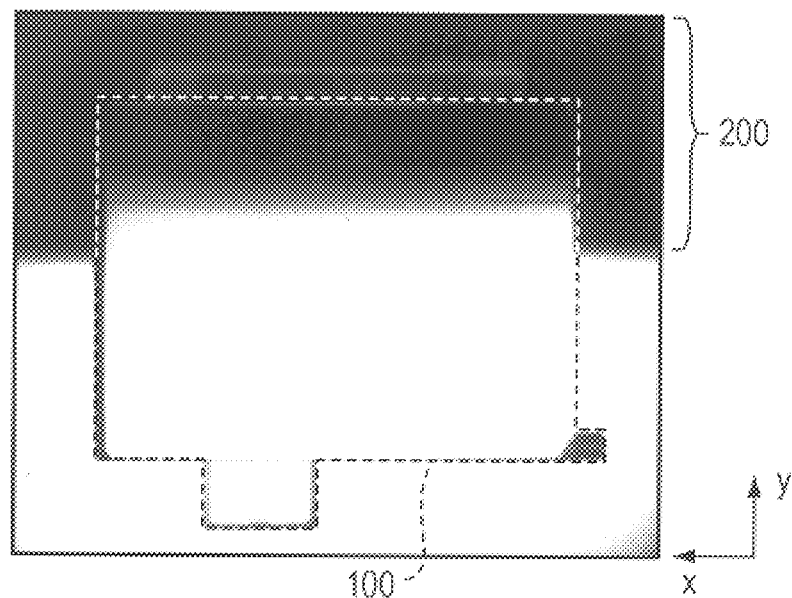
FIGS. 5a through 5e show image patterns when the diffuser unit in FIG. 1 is moved for adjustment.
Figure 5B:
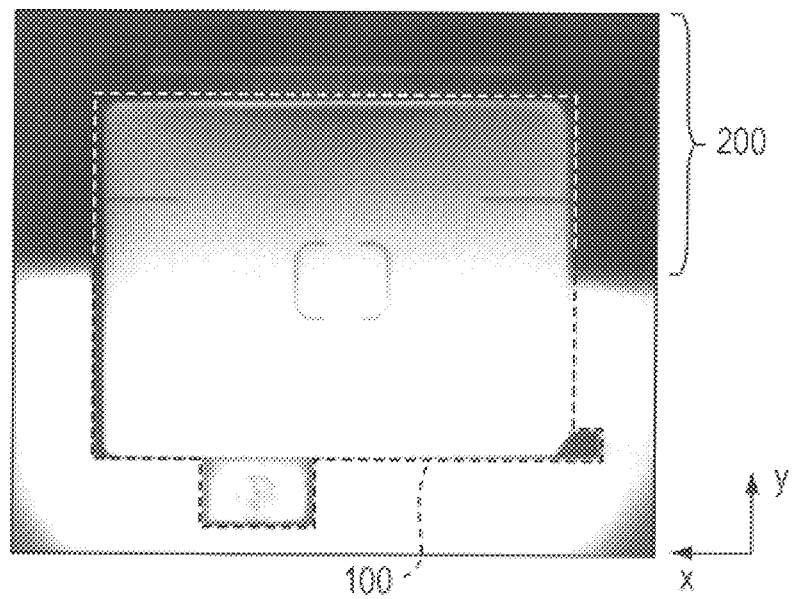

In the case when the focal point of the standard lens is positioned behind the diffuser plate 5, at the light guide fiber bundle 3 side, i.e., the distance between the standard lens and the diffuser plate 5 is smaller than the standard length, the shading image is formed as a real inverted image inside the image 100 as shown in FIGS. 5a and 5b. In this case, the smaller the distance is (i.e. the larger the distance from the standard length), the more distinct the shading image is. The shading image in FIG. 5a is more distinct than that in FIG. 5b because of the smaller distance.

Figure 5C:
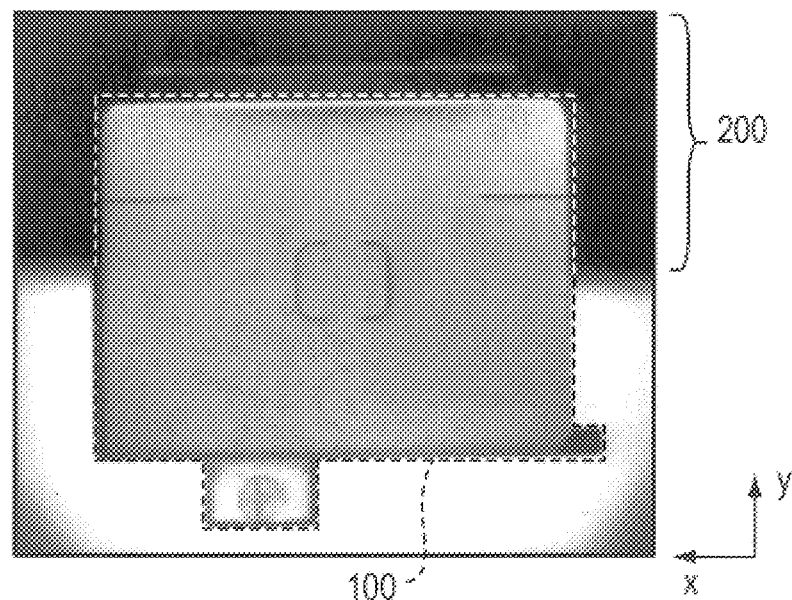

In the case when the focal point of the standard lens coincides with the diffuser plate 5, that is, the standard length for inspection, the brightness distribution inside the image 100 of the standard lens is uniform as shown in FIG. 5c.

Figure 5D:
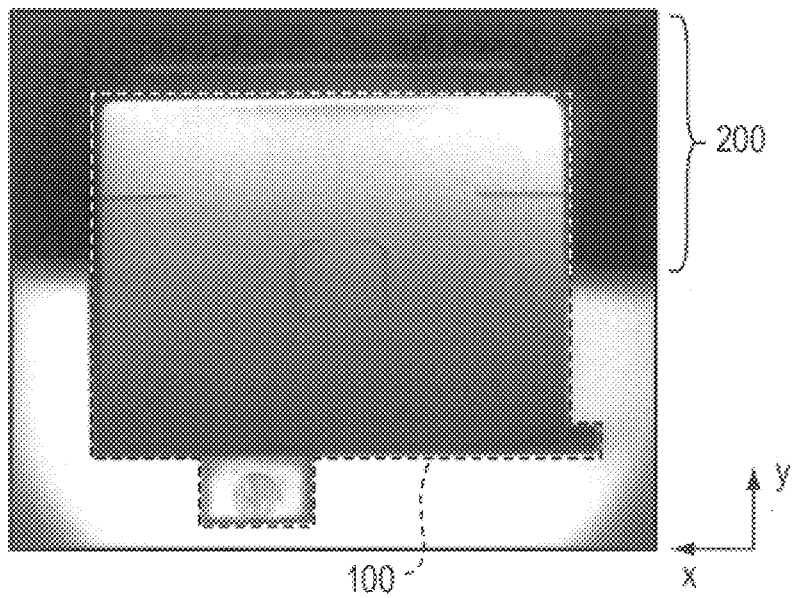
Figure 5E:
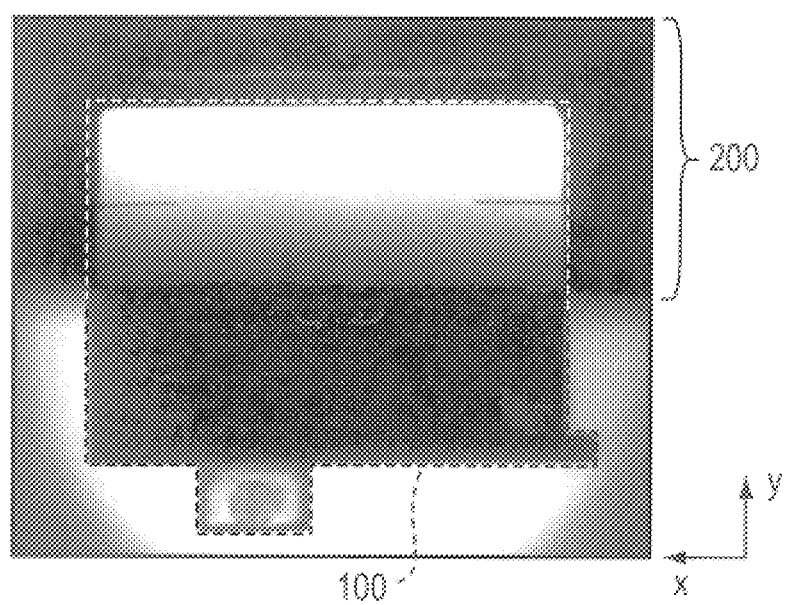

In the case when the focal point of the standard lens is positioned in front of the diffuser plate 5, at the image photographing unit 7 side, i.e., the distance between the standard lens and the diffuser plate 5 is larger than the standard length, the shading image of the light intercepting plate 6 is formed as a real correct image inside the image 100, as shown in FIGS. 5d and 5e. In this case, the larger the distance is (i.e. the larger the distance from the standard length), the more distinct the shading image is. The shading image in FIG. 5e is more distinct than that in FIG. 5d because of the larger distance.

Accordingly, the illumination unit 4 can be manually adjusted to ensure that the focal point of the standard lens coincides with the diffuser plate 5 based on the images displayed on the display 10.

During adjustment, if, as shown in FIG. 5a or 5b, the shading image in the image 100 appears in the same orientation as the image 200 of the light intercepting plate 6 outside the lens image 100, it means that the diffuser unit 4 is too close to the target lens. The diffuser unit 4 is thus moved away from the target lens. On the other hand, if, as shown in FIG. 5d or 5e, the shading image in the image 100 appears in an opposite orientation to the image 200 of the light intercepting plate 6 outside the lens image 100, it means the diffuser unit 4 is too far from the target lens. The diffuser unit 4 is thus brought closer to the target lens. When the shading image essentially disappears from the area within the image 100 as shown in FIG. 5c, the adjustment is stopped since the diffuser unit 4 will then be at the standard distance length.

Figure 6:
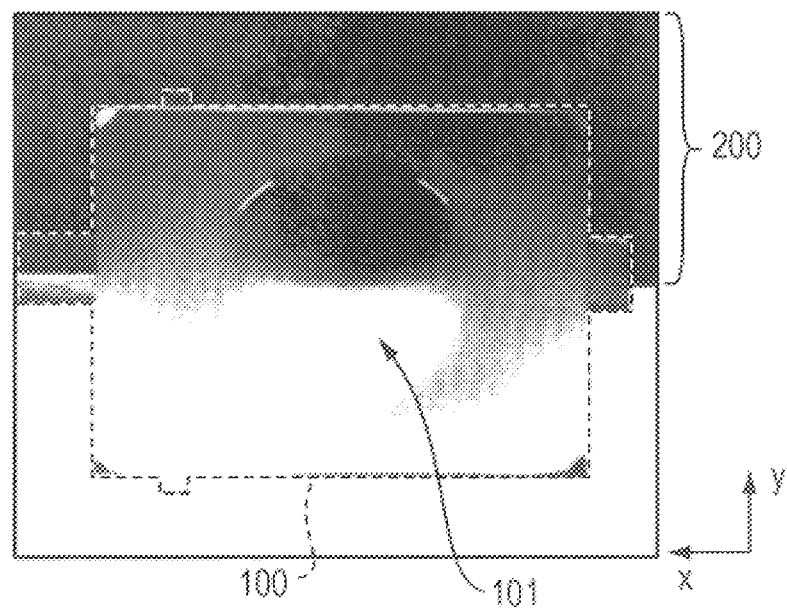
FIG. 6 shows the image pattern when an optical member with a sink mark is inspected.

After the adjustment process, the standard lens is replaced by an actual target lens. As a result of the adjustment, if the target lens is acceptable and has no defects, the brightness distribution inside the image 100 is uniform. However, if the target lens has an inhomogeneous refractive power distribution due to a refractive index anomaly or a shape defect at the surface, the focal length at the anomalous part will differ from the focal length at the normal part. Thus, as shown in FIG. 6, an anomaly image 101 of the light intercepting plate 6 will appear at the anomalous part.

After the adjustment of the diffuser unit 4a along the rotation axis Ax, the centering process begins, in which the target lens A is aligned, so that the optical axis of the target lens A coincides with the rotation axis Ax, by controlling the X-Y stage 18. In the present embodiment, the centering process is automatically executed.

Figure 7:
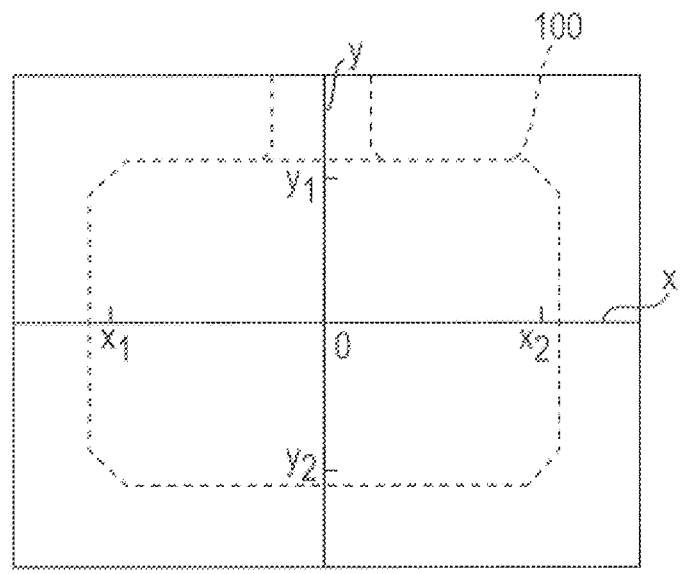
FIG. 7 shows the coordinate axes and coordinate positions defined on the image field.

Firstly, the principle used to find the deviation of the optical axis of the target lens A from the rotation axis Ax will be explained. The following principle is common to the first and second embodiments. FIG. 7 shows a definition of a coordinate system in the captured image field. An x axis and a y axis are defined which correspond to the definition of the x and y axes in FIG. 5a. The x and y axes intersect on an origin o which is the center of the field. Points x1 and x2 on the x axis and points y1 and y2 on the y axis are defined depending on the shape of the target lens so that these points are located on the peripheries of the lens image 100 such that these points are included in the outline of the lens image 100 when the target lens is centered.

After the adjustment process, since the focal point of the target lens A coincides with the diffuser plate 5, the light beams incident from any point on the diffuser plate 5 are parallel light beams at the photographing unit 7. The light detecting element 9 receives primarily the portion of light parallel to the optical axis. Therefore, when the optical axis of the target lens A coincides with the knife edge 6a, i.e., it coincides with the rotation axis Ax, the brightness within the outline of the lens image 100 will become uniform regardless of the rotation angle of the knife edge 6a as long as there are no defects in the target lens A.

Also, when the optical axis of the target lens A deviates from the rotation axis Ax, the brightness within the outline of the lens image 100 will vary depending upon the rotation angle of the knife edge 6a. This occurs because, if the focal point of the target lens A is located on a part of the diffuser plate 5 where the light intercepting plate 6 is not mounted, the light beam from the focal point (which is the main component of the brightness within the lens portion) is incident into the target lens A, and the brightness in the outline of the lens image will be higher. On the other hand, if the focal point of the target lens A is located on the light intercepting plate 6, the light beam from the focal point is not incident into the target lens A and the brightness in the outline of the lens image will be lower.

Accordingly, since the difference of the brightness between the cases when the light intercepting plate 6 is located at a rotation angle of 0 degrees and 180 degrees varies in accordance with the deviation amount of the optical axis from the rotation axis Ax along the y axis, the deviation amount can be determined based on the difference of the brightness.

FIGS. 8 through 12 show actual captured image patterns when the optical axis of the target lens A varies from the rotation axis Ax along the y axis.

Figure 8A:
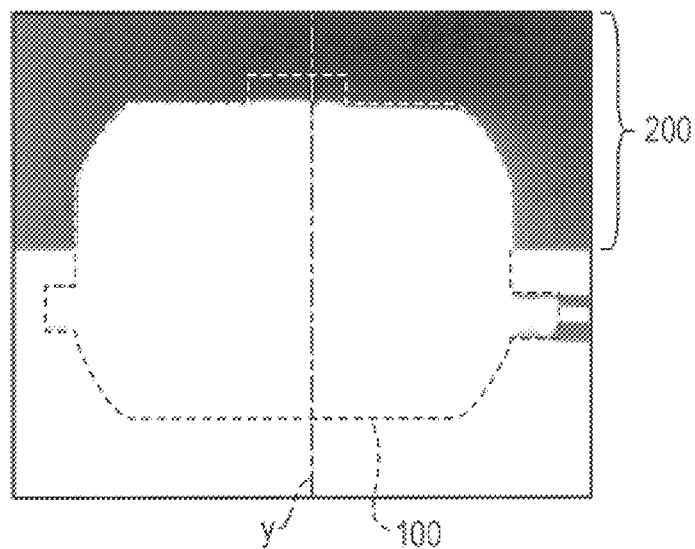
FIGS. 8a through 8d show image patterns and schematic drawings of the light intercepting plate and diffuser plate for the case where the amount of deviation is +0.2 mm in the y direction.
Figure 8B:
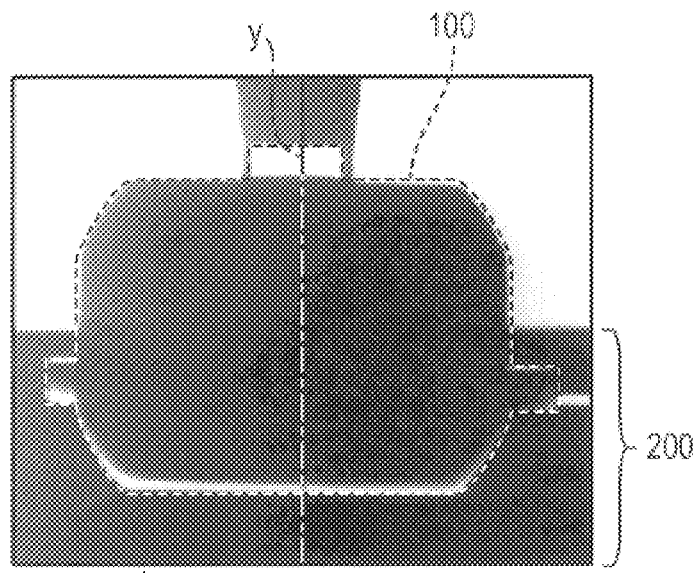
Figure 8C:
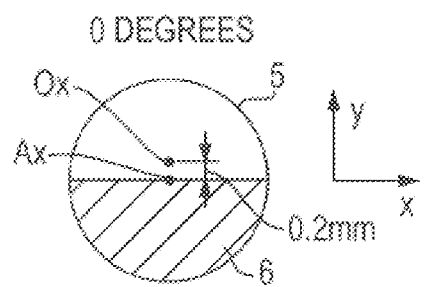
Figure 8D:
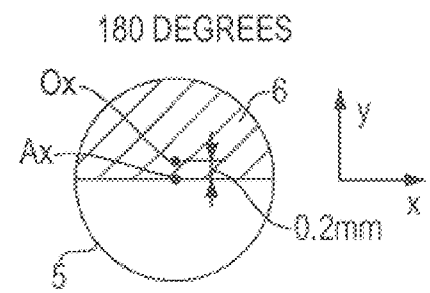

FIGS. 8a and 8b show images when the optical axis ox of the target lens A deviates from the rotation axis Ax by +0.2 mm along the y axis on the diffuser plate 5. FIG. 8a is the image pattern when the light intercepting plate 6 is in the standard position (rotation angle equal to 0 degrees). FIG. 8c shows the relationship between the light intercepting plate 6, the optical axis Ox of the target lens A, which coincides with the focal point, and the rotation axis Ax. As the focal point is located on the part of the diffusing plate 5 without the light intercepting plate 6 as shown in FIG. 8c, the brightness within the lens image 100 is higher, as shown in FIG. 8a. In this case, when the light intercepting plate 6 is located at a rotation angle of 180 degrees, since the optical axis Ox is included in the light intercepting plate 6 as shown in FIG. 8d, the brightness within the lens image 100 becomes lower, as shown in FIG. 8b.

Figure 13:
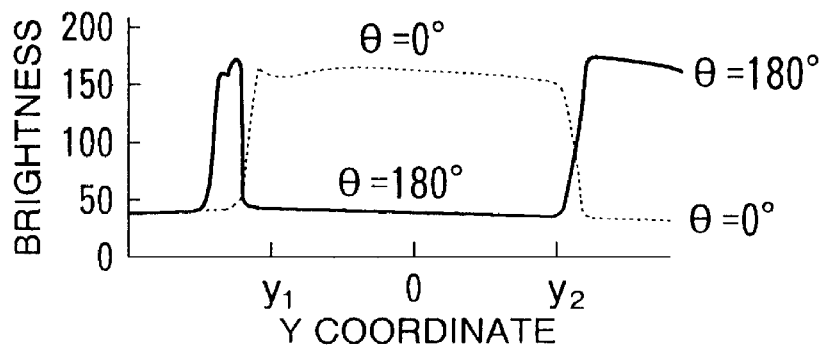
FIG. 13 is a graph which shows the brightness distributions along the y axis for the image data of FIG. 8.

The brightness distributions along the y axis in FIGS. 8a and 8b are shown in FIG. 13. The horizontal axis of FIG. 13 represents the position of the pixel along the y axis (y coordinate) and the vertical axis represents the digital brightness for each pixel. The broken line shows the brightness distribution at the standard position (0 degrees) and the solid line shows the same at the inverted position (180 degrees).

In order to obtain the brightness information within the lens image 100, excluding the peripheral portions of the lens image and the background image, the brightness data of the pixels between the coordinates y1 and y2 should be accumulated. Also, the brightness difference between the conditions at 0 degrees and 180 degrees can be obtained by subtracting the accumulated brightness data at 0 degrees form that at 180 degrees. The brightness difference varies in accordance with the deviation amount.

Figure 9A:
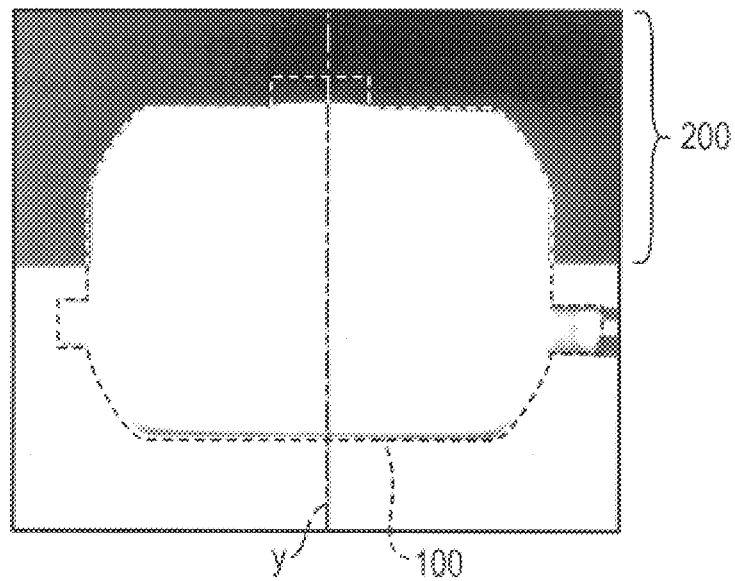
FIGS. 9a and 9b show image patterns for the case where the amount of deviation is +0.1 mm in the y direction.
Figure 9B:
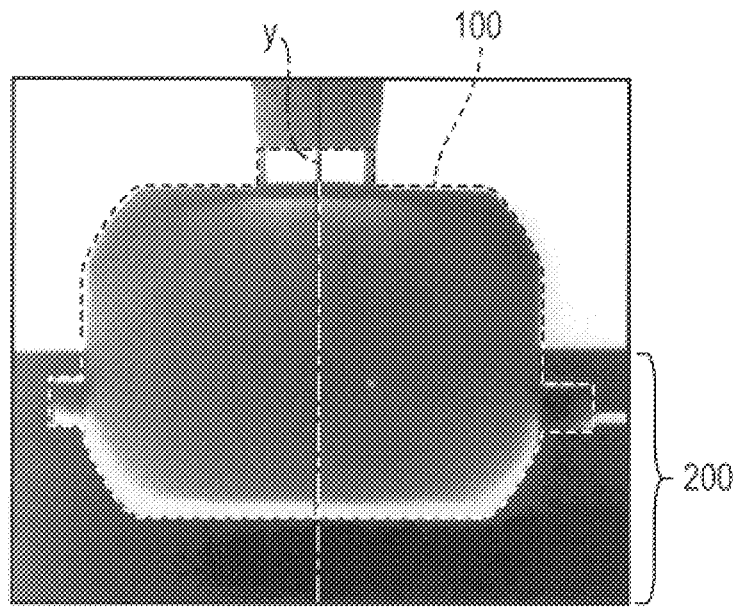

FIGS. 9a and 9b show images when the optical axis Ox of the target lens A deviates from the rotation axis Ax by +0.1 mm along the y axis on the diffuser plate 5.

Figure 14:
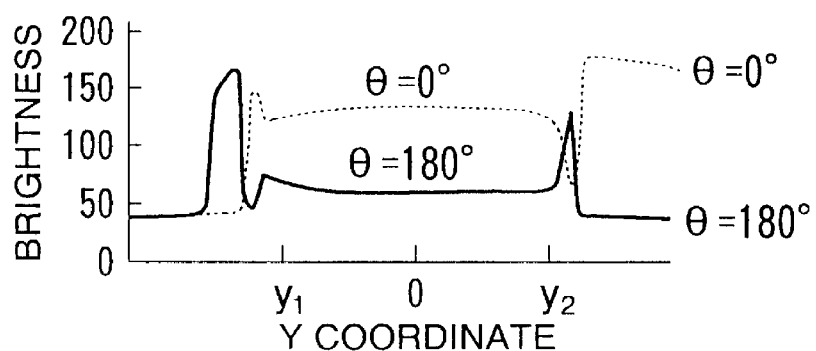
FIG. 14 is a graph which shows the brightness distributions along the y axis for the image data of FIG. 9.

FIG. 9a is an image when the rotation angle equals 0 degrees. The brightness within the lens image 100 is high. In this case, when the rotation angle equals 180 degrees, the brightness within the lens image 100 becomes low as shown in FIG. 9b. The brightness distributions along the y axis in FIGS. 9a and 9b are shown in FIG. 14. The brightness difference between the conditions at which the rotation angles are 0 degrees and 180 degrees is smaller than that of FIG. 13 because of the smaller deviation amount.

Figure 10A:
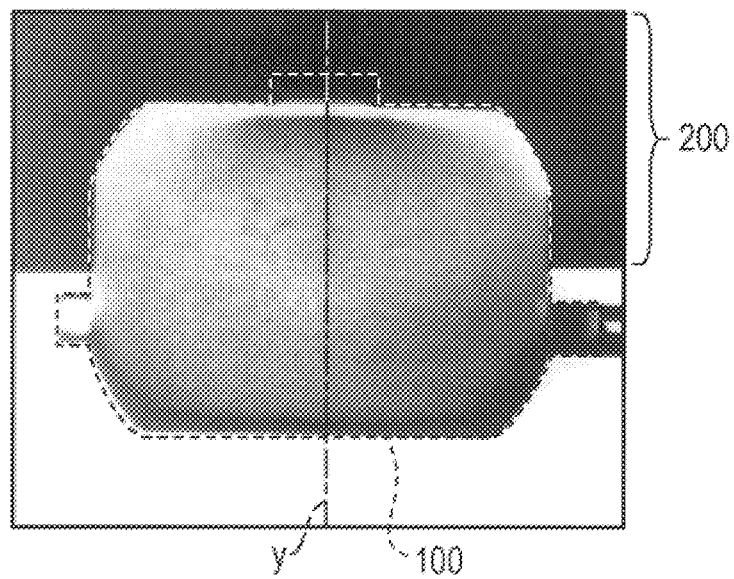
FIGS. 10a and 10b show image patterns for the condition where centering in the y direction has been performed.
Figure 10B:
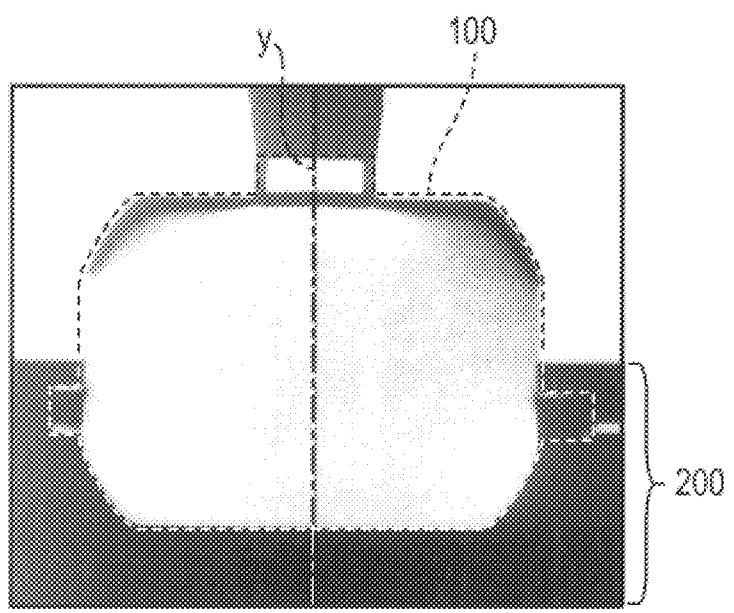

FIGS. 10a and 10b show images when the optical axis Ox of the target lens A coincides with the rotation axis Ax.

Figure 15:
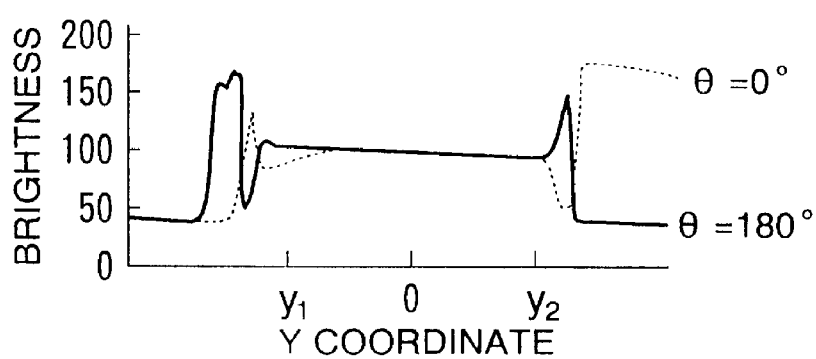
FIG. 15 is a graph which shows the brightness distributions along the y axis for the image data of FIG. 10.

FIG. 10a is an image when the rotation angle equals 0 degrees, while FIG. 10b shows an image when the rotation angle equals 180 degrees. The brightness distributions along the y axis in FIGS. 10a and 10b are shown in FIG. 15. The brightness distributions within the lens image 100 are almost identical in the range between the coordinates y1 and y2.

Figure 11A:
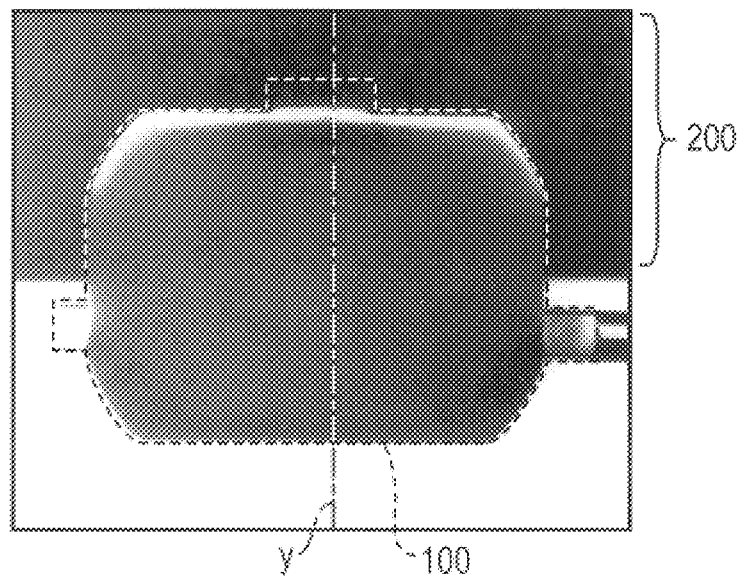
FIGS. 11a and 11b show image patterns for the case where the amount of deviation is −0.1 mm in the y direction.
Figure 11B:
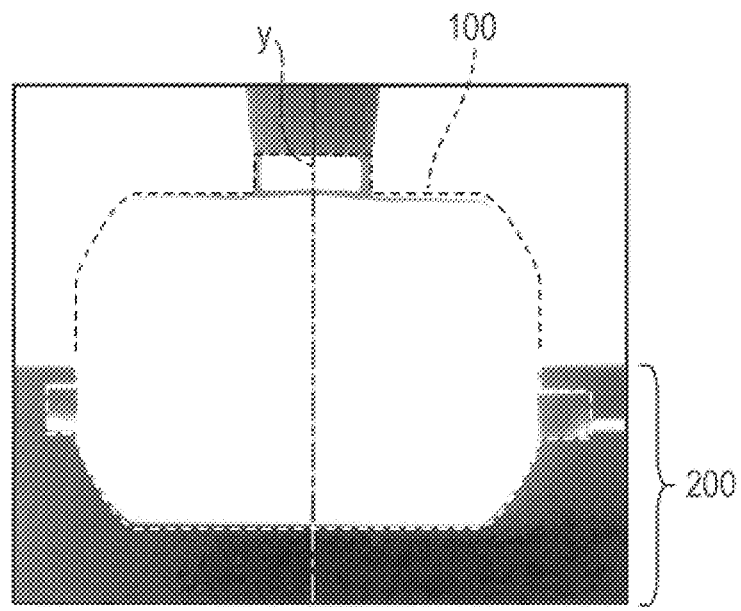

FIGS. 11a and 11b show images when the optical axis ox of the target lens. A deviates from the rotation axis Ax by −0.1 mm along the y axis on the diffuser plate 5.

Figure 16:
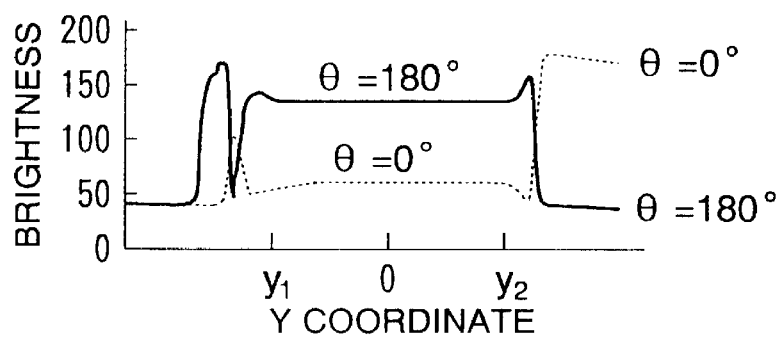
FIG. 16 is a graph which shows the brightness distributions along the y axis for the image data of FIG. 11.

FIG. 11a is an image when the rotation angle equals 0 degrees. The brightness within the lens image 100 is low. In this case, when the rotation angle equals 180 degrees, the brightness within the lens image 100 is high as shown in FIG. 11b. The brightness distributions along the y axis in FIGS. 11a and 11b are shown in FIG. 16.

Figure 12A:
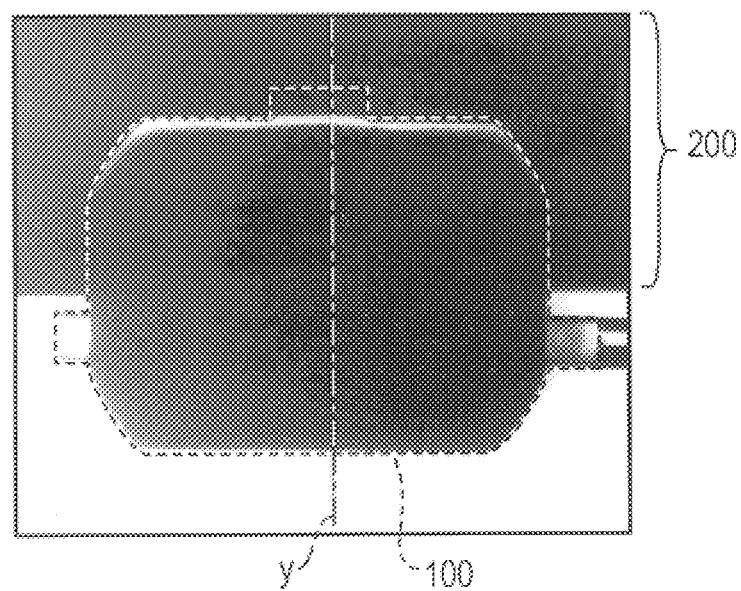
FIGS. 12a and 12b show image patterns for the case where the amount of deviation is −0.2 mm in the y direction.
Figure 12B:
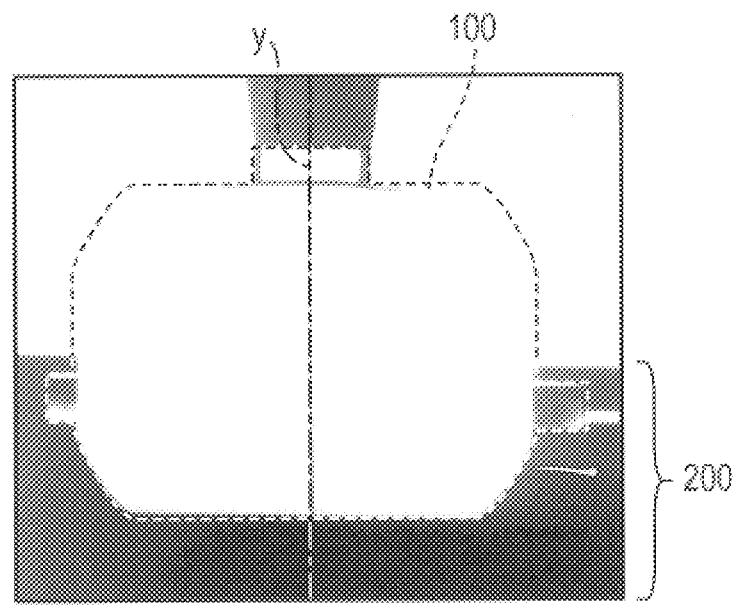

FIGS. 12a and 12b show images when the optical axis ox of the target lens A deviates from the rotation axis Ax by −0.2 mm along the y axis on the diffuser plate 5.

Figure 17:
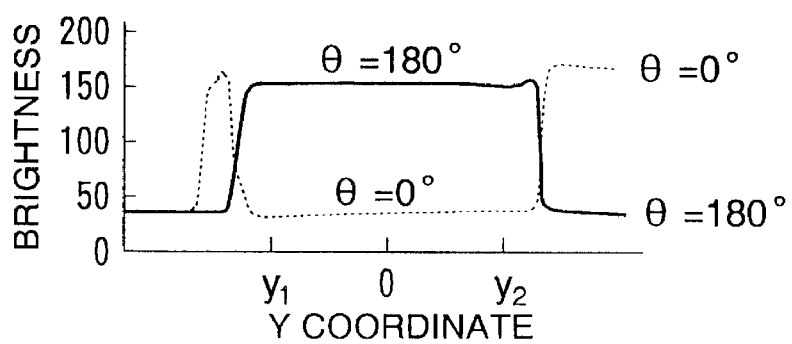
FIG. 17 is a graph which shows the brightness distributions along the y axis for the image data of FIG. 12.

FIG. 12a is an image when the rotation angle equals 0 degrees. The brightness within the lens image 100 is low. In this case, when the rotation angle equals 180 degrees, the brightness within the lens image 100 is high as shown in FIG. 12b. The brightness distributions along the y axis in FIGS. 12a and 12b are shown in FIG. 17. The brightness difference is larger than that of FIG. 16 because of the larger deviation amount.

The value of the brightness difference can be determined by subtracting the total brightness at 180 degrees from that at 0 degrees. The total brightness is calculated by accumulating the brightness data of the pixels from y1 to y2.

Figure 18:
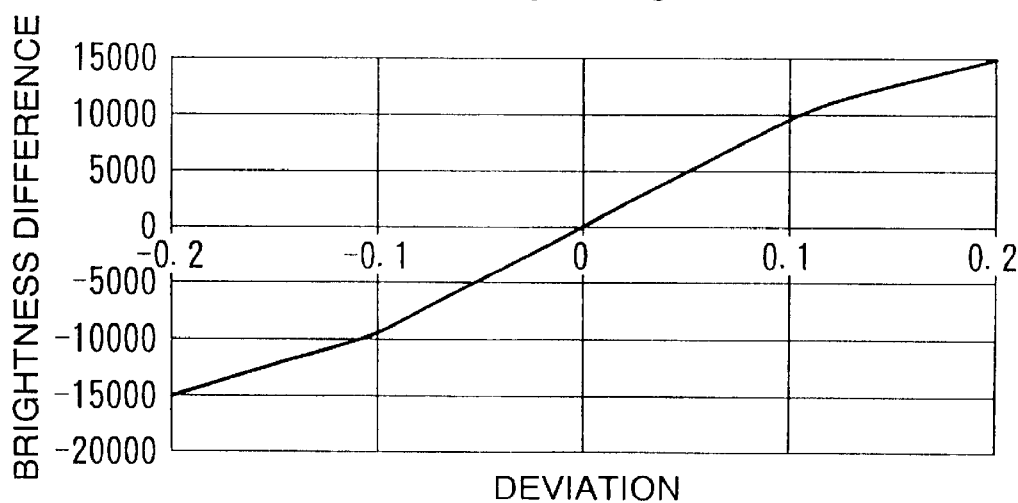
FIG. 18 is a graph showing the correspondence between the deviation and the brightness differences calculated from FIGS. 13 to 17.

FIG. 18 is a graph showing the relationship between the deviation amount and the brightness difference.

In accordance with the above relationships between the deviation and the brightness difference, and based on FIG. 18, it can be seen that the brightness difference is proportional to the deviation amount. The larger the deviation amount, the larger the value of the brightness difference. Thus, the deviation can be found by analyzing the brightness difference.

Only deviation along the y axis is described above, however, the same principle can also be applied to determining the deviation along the x axis.

In the first embodiment, the correspondence between the brightness difference and the deviation is found by using a standard lens with no defects in the calibration process. The detected correspondence is then stored in the reference data memory 16.

The calibration process must be performed for each kind of target lens. In the calibration process, a standard lens is set on the X-Y stage 18, and the diffuser unit 4 is adjusted along the rotation axis Ax in accordance with the adjustment process above. After that, the standard lens is manually centered so that the optical axis of the standard lens coincides with the rotation axis Ax. The manual centering can be executed by observing the brightness difference and adjusting until it is minimized.

After centering the standard lens, the image processing unit 14 instructs the X-Y stage controlling unit 17 to move the lens at 10 micrometer intervals along the +y axis until the total moving amount becomes 500 micrometers. At each step, the brightness data of the pixels along the y axis are detected for conditions where the rotation angles are 0 degrees and a 180 degrees. The brightness difference obtained at each step is divided by 64 and rounded to the nearest integer. The correspondence between the deviation and the brightness difference is obtained, for example, as shown in the following table 1.

TABLE 1

| Deviation (micrometer) | Brightness difference | Brightness difference Divided by 64 |
|---|---|---|
| 0 | 325 | 5 |
| 10 | 807 | 13 |
| 20 | 2019 | 32 |
| 30 | 3272 | 51 |
| 40 | 4462 | 70 |
| 50 | 5638 | 88 |
| 60 | 6711 | 105 |
| 70 | 7748 | 121 |
| 80 | 8656 | 135 |
| 90 | 9539 | 149 |
| 100 | 10503 | 164 | since the resolution of the pulse motors for moving the X-Y stage 18 is 10 micrometer per pulse, the divided brightness difference corresponds to the pulse count of the motor 20 or 21 of the X-Y stage 18. The following table 2 shows the correspondence between the divided brightness difference due to deviation and the pulse count to correct the deviation.

TABLE 2

| Brightness difference Divided by 64 | Pulse count for correction |
|---|---|
| 1–12 | 0 |
| 13–31 | 1 |
| 32–50 | 2 |
| 51–69 | 3 |
| 70–87 | 4 |
| 88–104 | 5 |
| 105–120 | 6 |
| 121–148 | 7 |
| 149–... | 8 |

The correspondence defined in the table 2 is stored in the reference data memory 16 and is used in the centering process for the actual target lens.

Although the table 2 only defines the pulse count for correcting deviations along the +y axis, deviations along the −y axis can be obtained to invert the direction of movement using the same pulse count. Also, the correspondence of the pulse count and deviations along the x axis will also be determined by a similar calibration process.

In the centering process of the first embodiment, the image processing unit 14 compares the detected brightness difference, which is a difference between the total brightness at 0 degrees and 180 degrees, with the values stored in the reference date memory 16 in order to find the pulse count corresponding to the brightness difference, along either of the x and y axes, with reference to the table data such as the table 2 stored in the reference data memory 16. Then, the image processing unit 14 instructs the X-Y stage controlling unit 17 to drive the pulse motors 20 and 21 by the appropriate pulse count. As a result of the centering process, the target lens A will be positioned at a position where the optical axis of the target lens A and the rotation axis Ax are coaxial.

Figure 19:
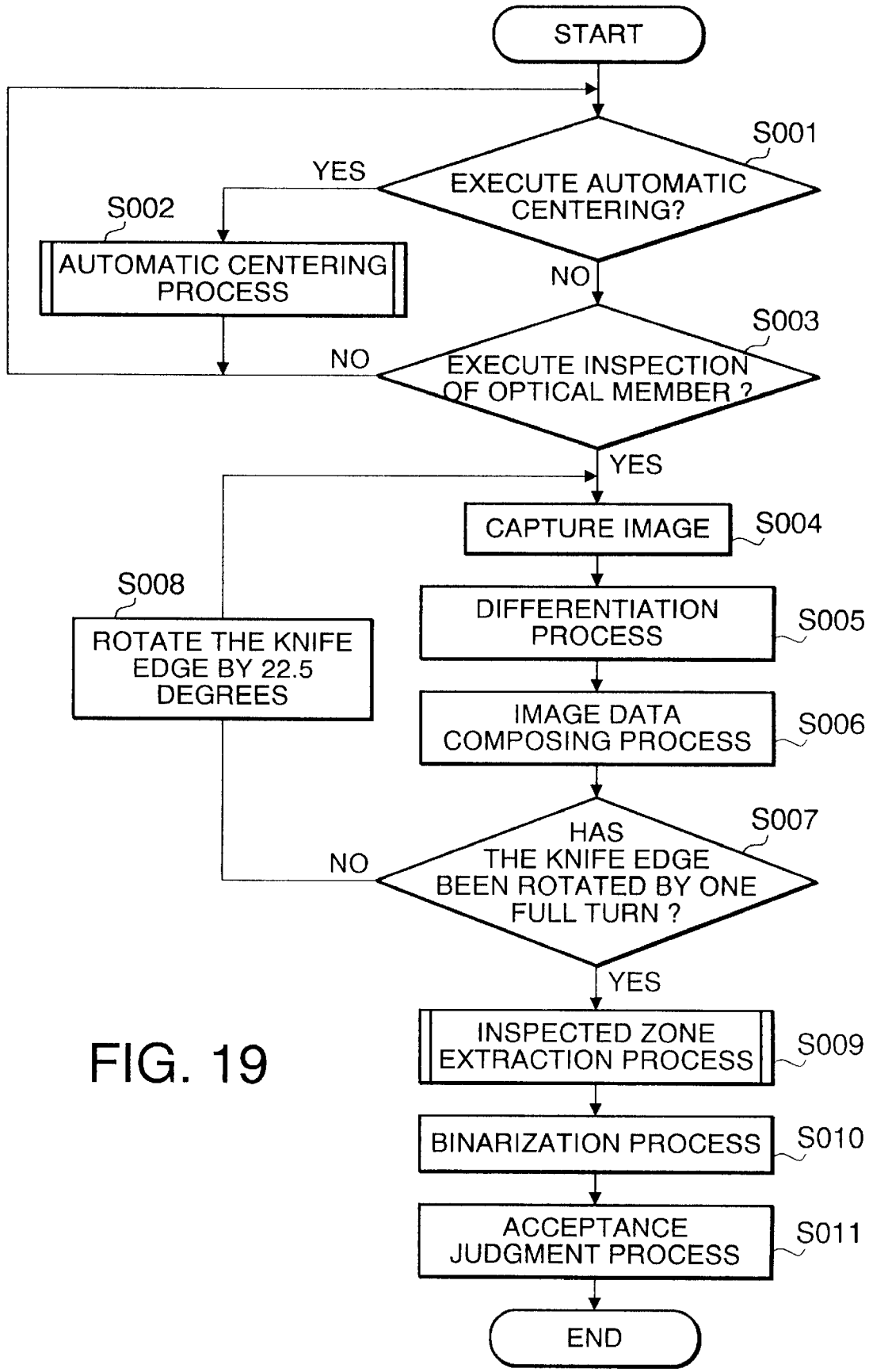
FIG. 19 is a flowchart which shows the main process executed in the image processing unit of FIGS. 1 and 2.

FIGS. 19 through 22 are flow charts describing the operation of the first embodiment. FIG. 19 is a main flow chart, FIGS. 20 and 21 describe the automatic centering process executed in step S002 in the main flow chart and FIG. 23 describes an inspected zone extraction process executed in step S009 of the main flow chart.

The main process of FIG. 19 starts when the power of the apparatus is turned ON. At steps S001 through S003, it is determined whether the automatic centering process is required and whether the inspection process is required. If the automatic centering process is required, i.e. the user has depressed the centering switch (not shown), this process is executed in step S002. If the inspection process is required, i.e. the user has depressed the start switch (not shown), the inspection process (the steps following step S003) is executed.

In the steps S004 through S006, the captured image data from the image detecting element 9 is converted into digital image data having 8-bit (256) gradations, and the converted image data is differentiated and composed into a composite image. Steps S004 though S006 are repeated until the knife edge 6a rotates by one full turn at intervals of 22.5 degrees (Steps S007 and S008).

At step S004, the analog output from each of the pixels of the captured image data is converted into the brightness data having 8-bit gradations and stored in the first memory 14a.

At step S005, a differentiation process is performed on the brightness data of each pixel stored in the first memory 14a.

That is, the difference between data of one pixel and the data of the adjacent pixels at the left and upper sides thereof is calculated and the absolute value of the difference is set as the differential value having 8-bit gradations of that one pixel. The differentiation process functions as a high pass filter to stress the edge portions of an image, where the brightness changes abruptly, so that the outlines of the target lens, the defect portions, and the edge of knife edge 6a are displayed in high contrast.

In the image composing process in step S006, the image processing unit 14 sums each of the differential values using the two memories 14a and 14b. That is, the first differential values are stored into the second memory 14b. When differential values for previous image data are already stored in the second memory 14b, the present differential value is added with the previous differential value and the composite value is then stored into the second memory 14b.

As a result of repeating the loop including steps S004 through S008 sixteen times, defect portions of the target lens in all directions are composed into a composite image.

If the target lens has a rotationally symmetrical refractive power anomaly or the target lens is a symmetrical aspherical lens, a partial image of the knife edge 6a appears as shown in FIG. 6. In the embodiment, these kinds of image of the refractive power anomalies cannot be detected automatically, since a plurality of images are composed while rotating the knife edge 6a and the image of knife edge 6a will be averaged out over a full rotation. However, in these cases, the user will be able to identify the anomaly on the display 10 based on an image that is not composed.

After the process of the loop of steps S004 through S008 is completed (YES at step S007), an inspected zone extraction process is executed at step S009. This process extracts or selects the effective zone of a lens from the entire image captured by the image detecting element 9.

At step S010, the composed differential data is converted into 1 bit digital data, i.e. is binarized, using an appropriate threshold level. The data for each pixel is classified into a white portion with a value of 255 or a black portion with a value of 0. Also, predetermined characteristic graphic quantities, such as area, maximum length, gravity point, Feret's diameter, and the like for the white portions are calculated based on the binary converted image. For example, the area is determined by counting the number of white level pixels.

Finally, the acceptance judgment process is executed at S011. That is, each of the characteristic graphic quantities calculated at S010 is compared with corresponding set of predetermined acceptance criterion values. The optical member is then determined to be unacceptable (defective) if there is even one characteristic graphic quantity that exceeds the range for the corresponding acceptance criterion value. The characteristic graphic quantities that are to be used for acceptance judgment are predetermined according to the type of the target lens. The main process ends when this acceptance judgment process ends.

The steps S004 through S011 comprise the inspection process as described above.

Figure 20:
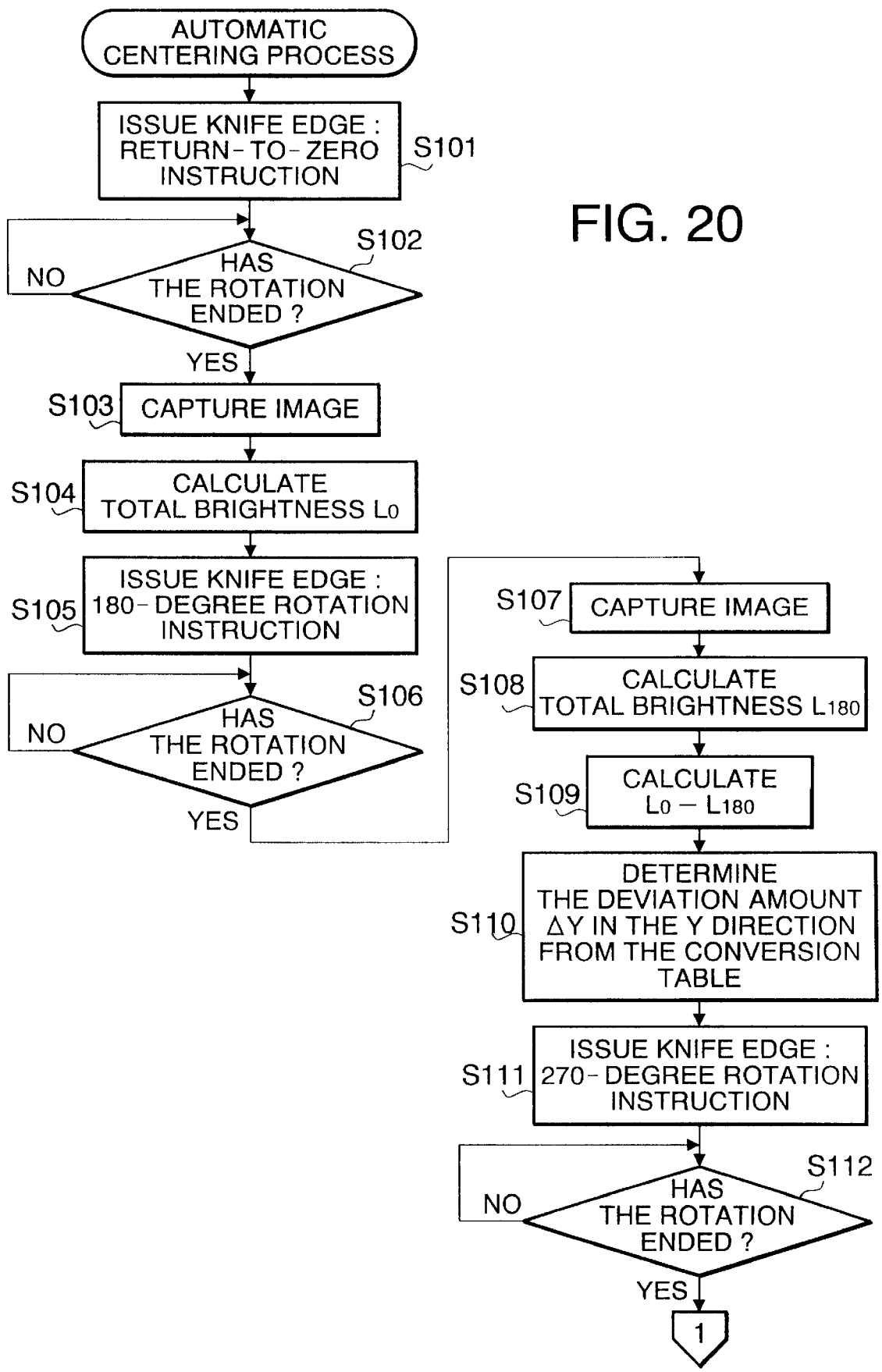
FIGS. 20 and 21 are flowcharts which show the automatic centering process executed at S002 of FIG. 19.
Figure 21:
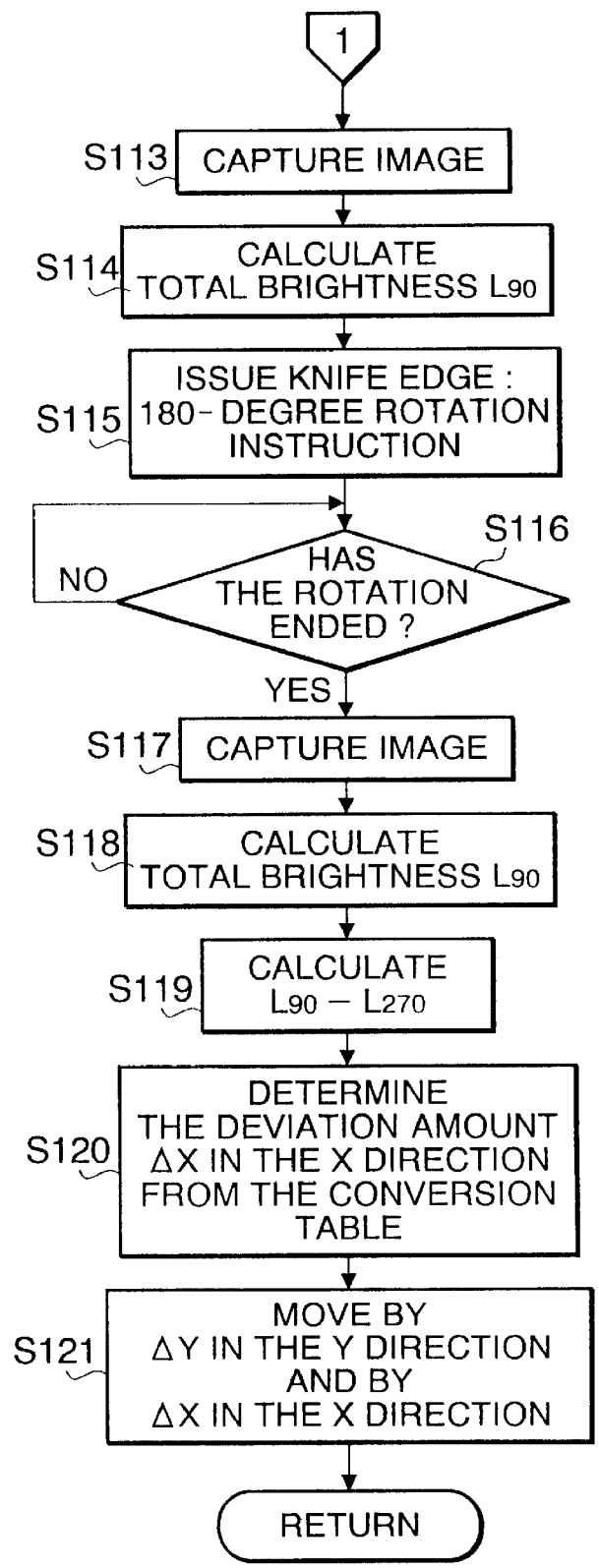

The automatic centering process executed in step S002 of the main process is shown in FIGS. 20 and 21.

The image processing unit 14 determines the deviation amount along the y axis in steps S101 through S110 and that along the x axis in steps S111 through S120 and instructs the X-Y stage controlling unit 17 in order to correct the deviations at step 121.

Initially, a return-to-zero instruction is issued to the knife edge rotation controlling unit 15 in step S101. Upon receiving this instruction, the knife edge rotation controlling unit 15 drives the knife edge rotating motor 13 and causes the knife edge 6a to be positioned at a rotation angle of 0 degrees as shown in FIG. 3, that is, the light intercepting plate 6 is positioned at the left side in FIGS. 1 and 2. When the knife edge 6a is determined to be set in the standard position in step S102, an image is captured to detect the brightness distribution along the y axis at step S103 and the total brightness L0 along the y axis is calculated in step S104. Then, the knife edge 6a *is rotated by* 180 degrees in steps S105 and S106, and the total brightness L180 along the y axis is calculated (step S108) based on the image captured in step S107. In step S110, the deviation amount $\Delta Y$ along the y direction is determined from the brightness difference, calculated in step S109, with reference to the correspondence data stored in the reference data memory 16.

At steps S111 and S112, the knife edge 6a rotates by 270 degrees such that it is set at a rotation angle of 90 degrees. After that, the deviation amount $\Delta X$ along the x direction is determined in steps S113 through S120 in the same manner as the deviation amount $\Delta Y$ was determined in steps S103 through S110.

At step S121, the X-Y table 18 is driven using the pulse data from the reference data memory 16 in order to coaxially align the optical axis of the target lens and the rotation axis Ax.

The inspected zone extraction process from step S009 of FIG. 19 is described with reference to FIGS. 22 and 23a through 23d.

In this process, the composed differential image data obtained by steps S004 through S008 of FIG. 19 is binarized in step S201 and closed zones are extracted in step S202. For the image data in the extracted zone, a hole filling process, a zone selection process and an AND operation process are executed in steps S203, S204 and S205. The binarization process is identical to step S010 of FIG. 19. Each of the other processes are described below.

Figure 23A:
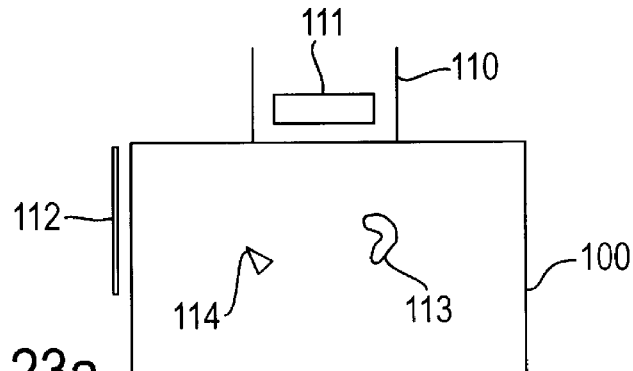
FIGS. 23a through 23d are explanatory diagrams of the inspected zone extraction process of FIG. 22.

As a result of the binarizing process, image data such as that shown in FIG. 23a is obtained. This figure shows the lens image 100, an image 110 of runner 19, an image 111 of a pattern on the runner, an image 112 of a gate, an image 113 of a refractive index anomaly such as jetting, and an image 114 of a piece of debris attached to the surface of the target lens. The images shown in FIGS. 23a through 23d are shown with white and black inverted for the purposes of illustration.

Figure 23B:
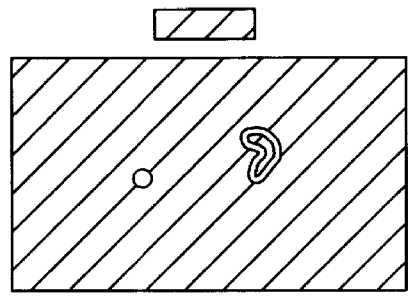

The closed zone extraction process is a process in which only the zones that are surrounded by closed white level lines (black lines in the figures) formed of white level pixels are extracted. The black level pixels which are surrounded by white level pixels are deemed to be pixels within the closed zone. The numerical values of all pixels deemed to be inside this closed zone are set to 255 while the numerical values of the pixels representing the border are set to 0. FIG. 23b shows the result of the closed zone extraction process. As shown in FIG. 23b, the lines 110 and 112, which are open at one end, are eliminated. Since the inversion of the white and black colors only occurs inside the lens periphery 100, which is a closed curve, the closed curves 113 and 114 in the interior remain.

Figure 23C:
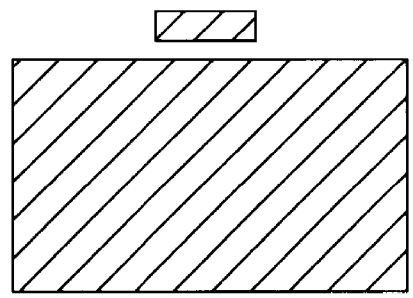

The hole filling process is for eliminating the black level pixels remaining within the white level pixels. FIG. 23c shows the image data obtained as a result of this hole filling process. As shown in FIG. 23c, the closed curves 113 and 114 inside the lens periphery 100 are eliminated and only the two zones 100 and 111, which are respectively large and small, remain.

Figure 23D:
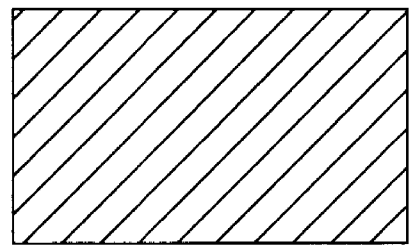

The zone selection process is for selecting only the zones which are deemed to be essential and deleting other closed zones. In this embodiment, the zone having the largest area is selected. FIG. 23d shows the image data obtained as a result of this zone selection process. Since the zone of white level pixels in this image corresponds to the zone of the image of the target lens, this image shall be referred to hereinafter as the "mask image".

The AND operation is performed between the 1 bit digital value of each pixel comprising the mask image and the 8-bit digital value of each pixel written into second memory 14b. That is, the 8-bit digital value of a pixel of the image data is multiplied by the 1 bit digital data of the corresponding pixel of the mask image. As a result of this AND operation, only the parts of the image data which overlap with the mask image will remain and the values of the other pixels will be set to 0.

Second embodiment

Figure 24:
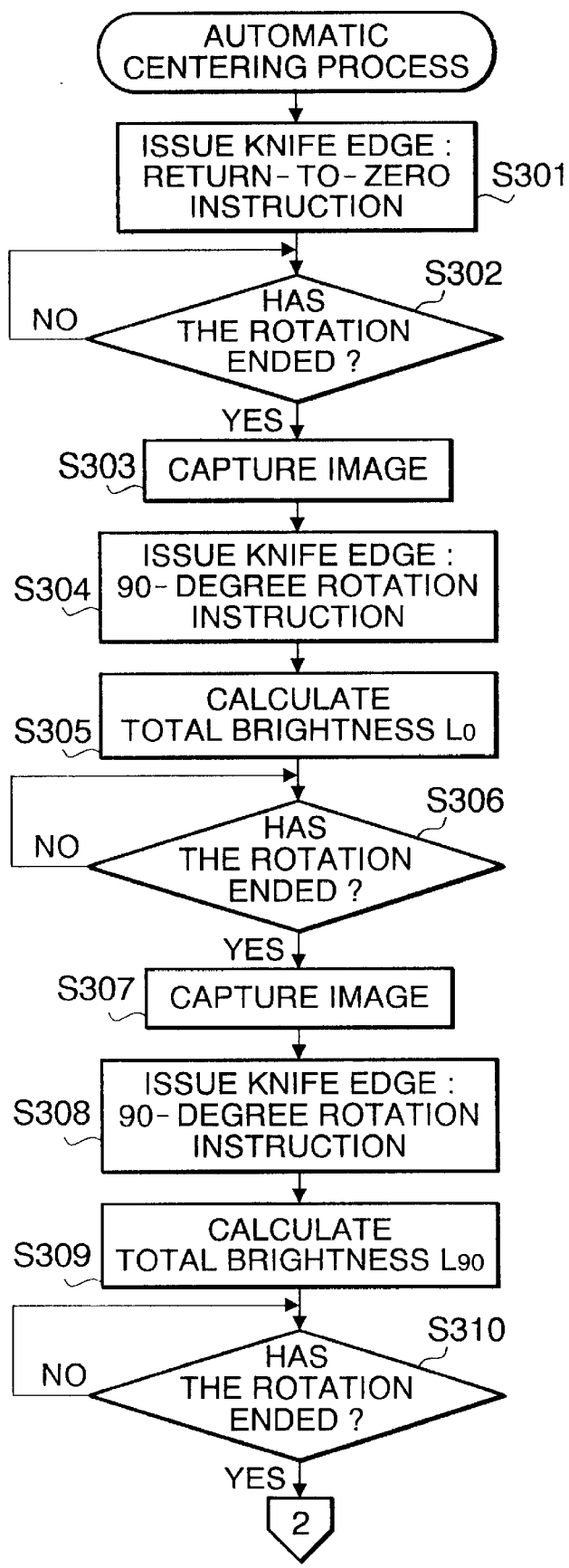
FIGS. 24 and 25 are flowcharts which show the automatic centering process of the second embodiment executed at S002 of FIG. 19.
Figure 25:
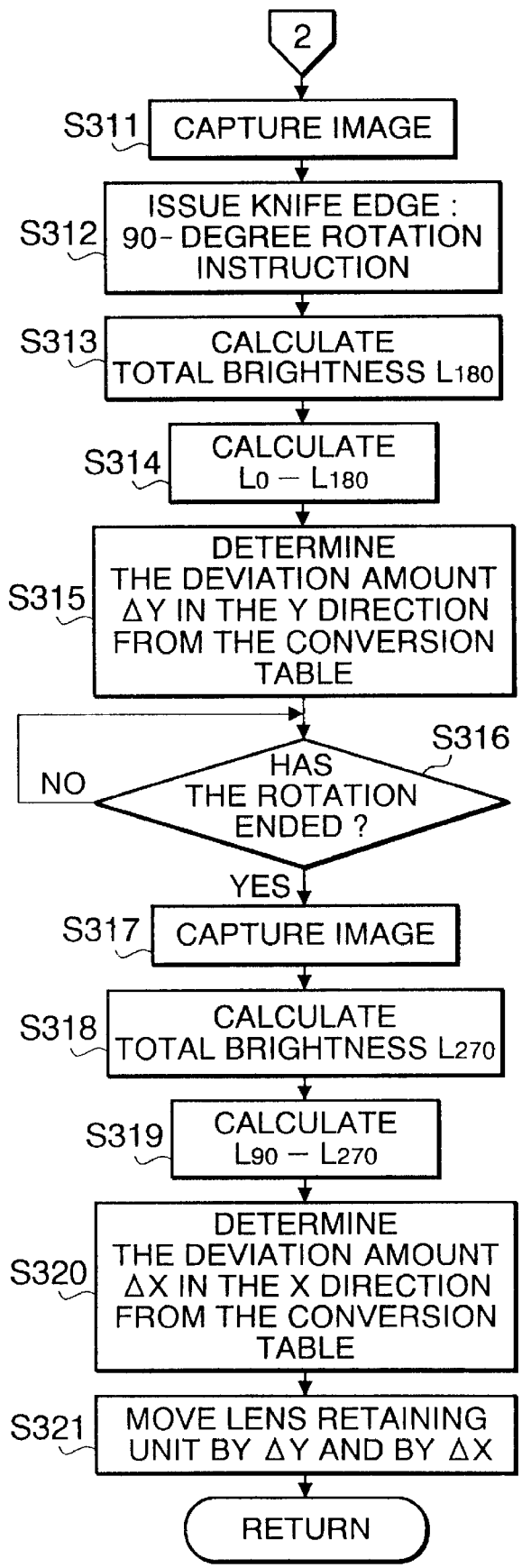

The second embodiment of the present invention differs from the first embodiment described above only in the content of the automatic centering process executed at S002 in FIG. 19 and is otherwise the same as the first embodiment. In the second embodiment, the centering process is different in that the knife edge 6a rotates at 90 degrees intervals and data processing is executed during, rather than after, the period when the knife edge 6a is rotating. The automatic centering process of the second embodiment is described by the flow charts in FIGS. 24 and 25.

In steps S301 and S302, the knife edge 6a is set in the standard position (rotation angle equals 0 degrees). In this condition, an image is captured at step S303 and immediately following the image capture, the knife edge 6a starts to rotate. During the period until the knife edge 6a rotates by 90 degrees, the total brightness L0 along the y axis is calculated in step S305.

When the knife edge 6a has rotated by 90 degrees (YES at step 306), the next image is captured at step S307. In a similar way, the total brightness L90 along the x axis is calculated during the next 90 degree rotation period (S308, 309 and S310).

At step 311, an image is captured when the knife edge 6a is set at a rotation angle of 180 degrees, and the knife edge 6a starts to rotate for the next 90 degrees rotation (step S312). Before the knife edge 6a reaches a rotation angle of 270 degrees, the total brightness L180 along the y axis is calculated (step S313), the brightness difference along the y axis is determined by subtracting L180 from L0 (step S314), and the deviation amount ΔY in the y direction is determined based on the brightness difference with reference to the correspondence data stored in the reference data memory 16 (Step S316).

When the knife edge 6a is set at a rotation angle of 270 degrees, the last image is captured at step 317, and the total brightness L270 is calculated in step S318. The brightness difference along the x axis is calculated by subtracting L270 from L90 at step S319. The deviation amount ΔX in the x direction is determined in the same manner as that for the y direction.

At step 321, the image processing unit 14 instructs the X-Y stage controlling unit 17 to drive the X-Y stage by the predetermined pulse values corresponding to the deviation amounts ΔY and ΔX.

In accordance with the second embodiment, since parallel processing is used for the rotation of the knife edge and the brightness calculation, the time required for inspection is reduced.

Third embodiment

In the first and second embodiments, the centering process is executed using the relationship between the deviation of the optical axis of the target lens from the rotation axis of the knife edge and the brightness difference. On the other hand, the apparatus of the third embodiment aligns an outline of the target lens so that a center of the outline is coaxial with the rotation axis. The initializing process to determine the coordinates of the rotation axis Ax in the captured image is required only in the third embodiment. The third embodiment is based upon the assumption that the optical axis of the target lens is located at the center of the outline thereof.

Here the "center of the outline" is defined as the center of the Feret's diameter of the frontal shape of the target lens. That is, the x coordinate of the center is determined as a middle point of the line along the x axis that covers the maximum width in the x direction, and the y coordinate of the center is determined as a middle point of the line along the y axis that covers the maximum width in the y direction.

When the target lens has a rotational symmetrical front shape, the gravity point of the lens coincides with the center of the outline. And therefore, in such a case, the target lens can be centered by ensuring that the gravity point coincides with the rotation axis Ax.

In the third embodiment, the initializing process is executed first, and then the standard lens is set to adjust the diffuser unit 4 along the rotation axis Ax in the adjustment process, which is identical to the first embodiment. After the adjustment process, the centering process and the inspection process are executed sequentially.

Figure 22:
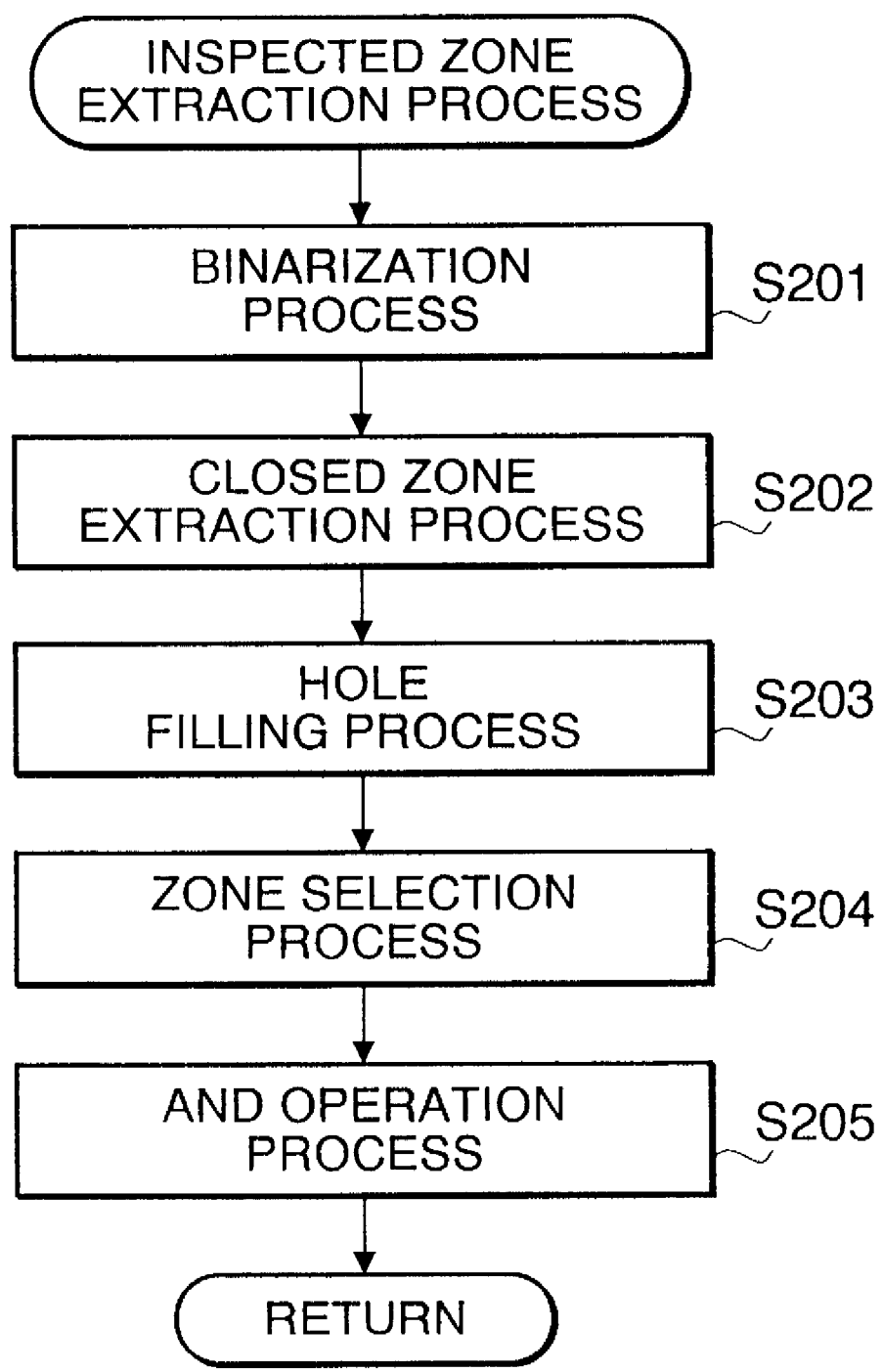
FIG. 22 is a flowchart which shows the inspected zone extraction process executed at S009 of FIG. 19.

Since the main process and the inspected zone extraction process of the third embodiment are identical to those of the first embodiment as shown in FIGS. 19 and 22, only the, non-identical portions, that is, the initializing process and the centering process are described below.

Figure 26:
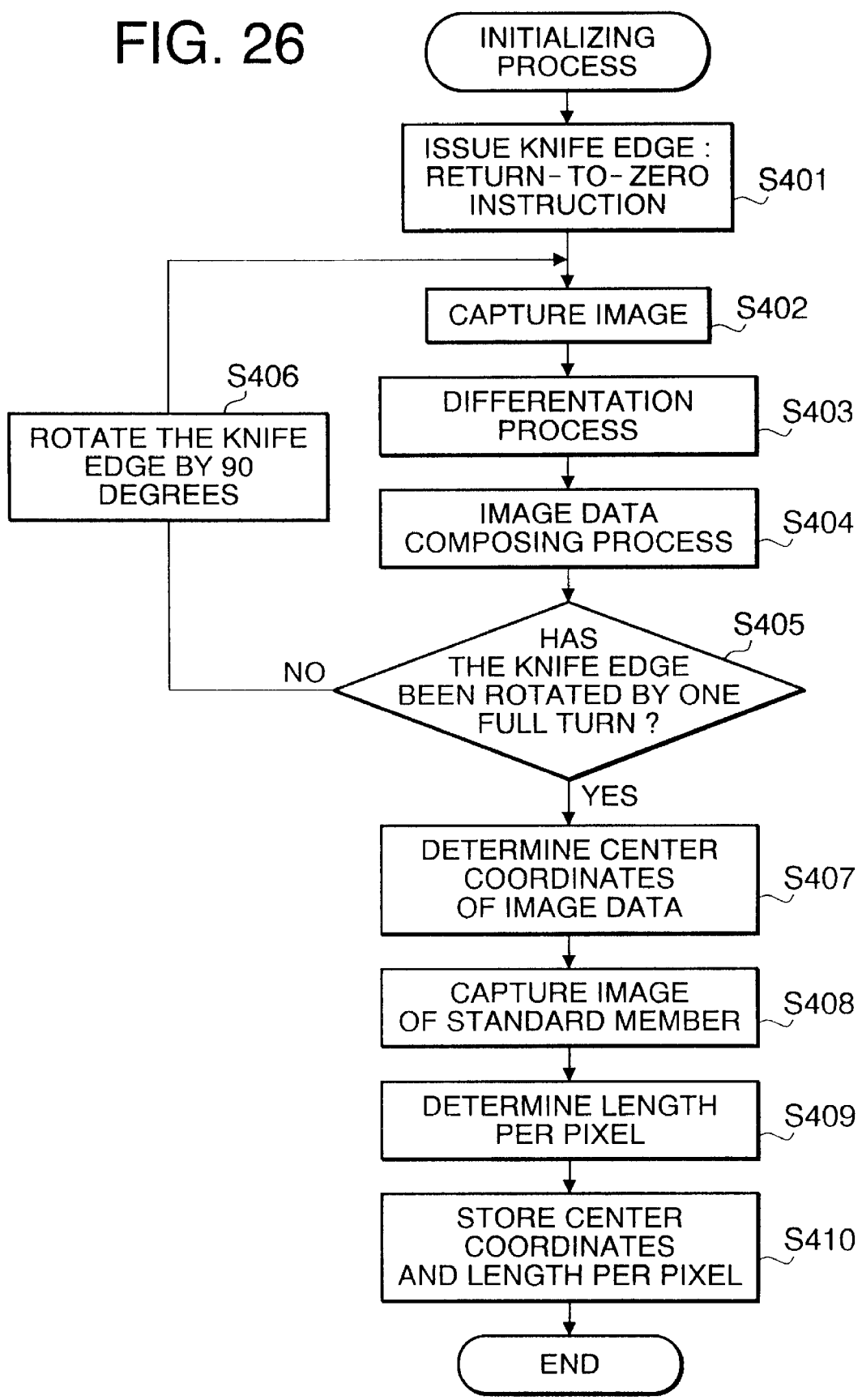
FIG. 26 is a flowchart which shows the initializing process of the third embodiment.

FIG. 26 is a flow chart describing the initializing process of the third embodiment. The initializing process starts when an initializing start switch (not shown) is turned ON. Next, predetermined basic data, i.e. the coordinate of the rotation axis Ax on the image field and the scale of the image formed on the image detecting element 9 are determined. The scale is defined as the length of a target lens that corresponds to one pixel of the image.

The initializing process is executed before a target lens is set on the holder 22. In step S401, a return-to-zero instruction is issued to the knife edge rotation controlling unit 15. Upon receiving this instruction, the knife edge rotation controlling unit 15 drives the knife edge rotating motor 13 and causes the knife edge 6a to be set at a rotation angle of 0 degrees as shown in FIG. 3, that is, the light intercepting plate 6 is positioned at the left side in FIGS. 1 and 2.

In steps S402 through S404, the captured image data from the image detecting element 9 is converted into image data having 256 gradations, and the converted image data is differentiated and composed into a composite image. Steps S402 though S404 are repeated until the knife edge 6a rotates by one full turn at 90 degrees intervals (S405 and S406). The differentiation process and the image composing process are identical to steps S005 and S006 in FIG. 19.

Figure 27:
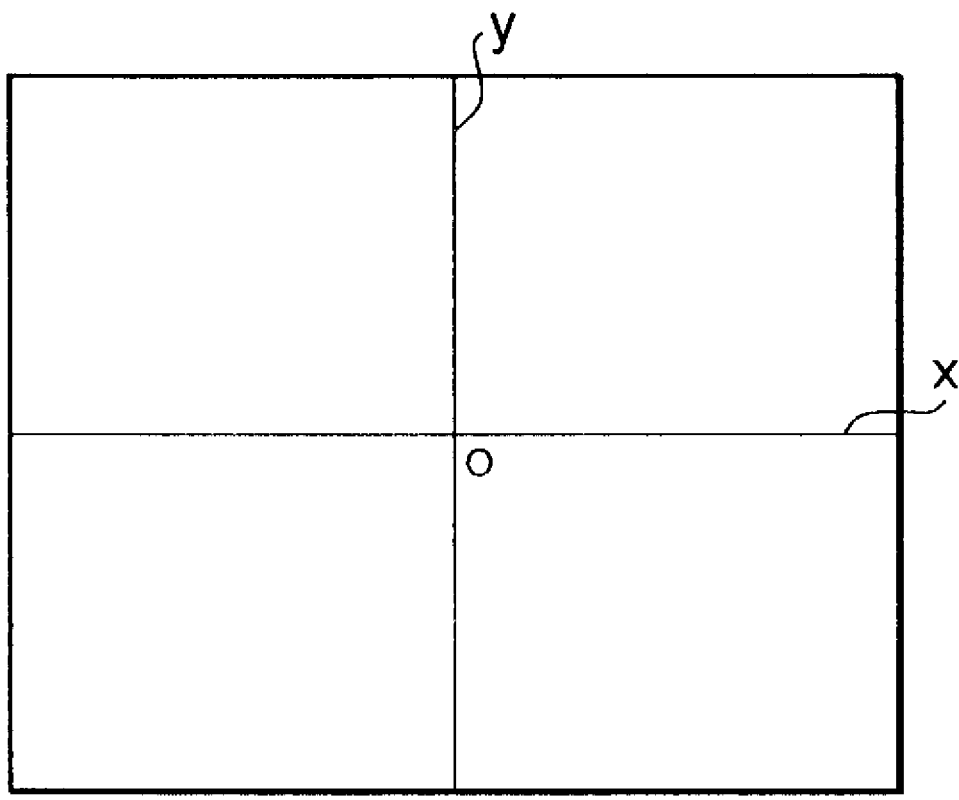
FIG. 27 is a field view of the captured image to define the x-y coordinates.

As a result of repeating the loop S402 through S406 at four times, the composite image data represents two liner axes x and y in the image field as shown in FIG. 27. The x axis is formed by the differential images of the knife edge 6a when it is at 0 degrees and 180 degrees and the y axis is formed by the differential images of the knife edge 6a when it is at 90 degrees and 270 degrees.

In steps S407 through S410, the center coordinate and the scale are determined. The center coordinate, which coincides with the rotation axis Ax, is determined as the position of the pixel at which the x and y axes intersect (step S407).

In step S408, a standard lens having a known length is mounted on the X-Y stage 18 so that the standard lens is located in the optical path between the illumination unit 4 and the photographing unit 7, and image data for the standard optical member is captured.

The scale is determined as a length per pixel. The length per pixel is determined by dividing the known actual length of the standard optical member by the number of pixels corresponding to the length of image of the standard optical member on the image field of the image detecting element 9 (step S409). The determined center coordinate and the length per pixel are stored in the reference data memory 16 in step S101.

Figure 28:
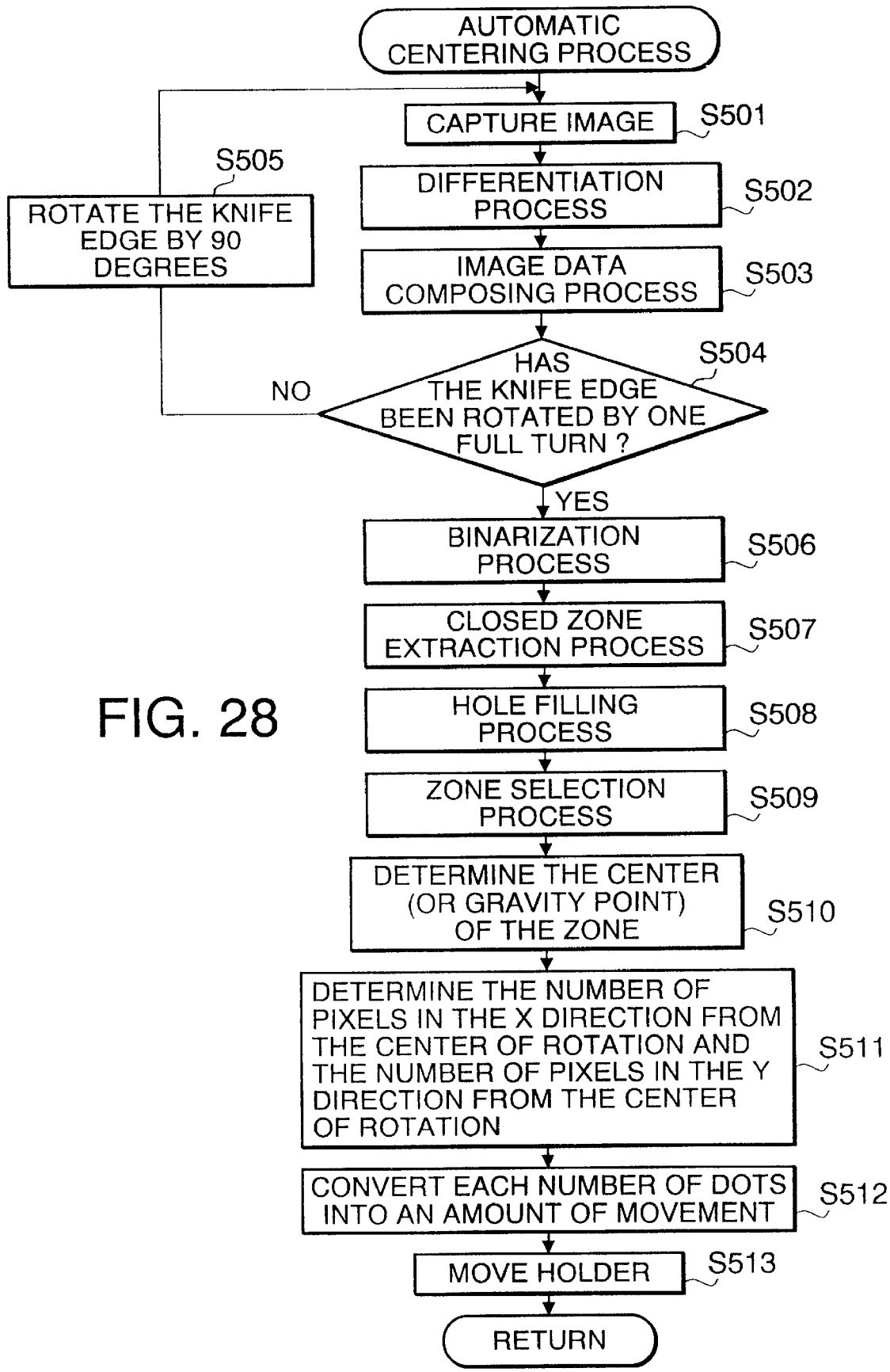
FIG. 28 is a flowchart which shows the automatic centering process of the third embodiment.

FIG. 28 is a flow chart describing the automatic centering process of the third embodiment, executed at S102 of the main flowchart in FIG. 19.

In steps S501 through S505, lens images, including defects, are obtained. Although the content of these steps are identical to steps S402 through S406 in FIG. 26, the target lens, rather than a standard lens, is set in the centering process.

The processes in steps S506 through S509 produce the mask image as described in steps S201 through S204 of FIG. 22.

The center of the Feret's diameter of the target lens or the gravity point of the target lens (when the gravity point coincides with the optical axis thereof) is determined based on the mask image of the target lens at step S510.

Then, the deviation of the center from the rotation axis Ax is determined as a number of pixels in either of the x and y directions at step S511. In step S512, the deviations represented by the number of pixels are converted into an actual length (micrometers) by using the scale determined in the initializing process and the X-Y stage is driven by the determined deviation in step S513.

As a result of the movement of the lens in step S513, the target lens is centered such that the optical axis of the target lens is coaxial with the rotation axis Ax.

The present disclosure relates to subject matters contained in Japanese Patent Application Nos. HEI 7-255066 filed on Oct. 2, 1995, and HEI 7-257953 filed on Oct. 4, 1995, which are expressly incorporated herein by reference in their entirety.

What is claimed is:

1. An optical inspecting apparatus for detecting a defect of an optical element to be inspected, said apparatus comprising:

means for illuminating an optical system including at least said optical element, said optical system having positive power;

means for intercepting a portion of the light emitted from said illuminating means, said light intercepting means being located between said illuminating means and said optical system so that a focal point of said optical system coincides with said light intercepting means, wherein a light transmitting portion and a light blocking portion of said light intercepting means are separated by a straight boundary line;

means for detecting an image of said optical element, said detecting means being located at an opposite side of said illuminating means with respect to said optical system;

means for rotating said light intercepting means about a rotation axis that intersects said straight boundary line;

means for moving said optical element in directions perpendicular to said rotation axis;

means for determining a deviation of said optical element from a standard position with respect to said rotation axis based on the image detected by said detecting means; and means for centering said optical element on said rotation axis by controlling said moving means in accordance with said deviation.

2. The optical inspecting apparatus according to claim 1, further comprising means for inspecting said optical, element based on a composite image composed of a plurality of images detected under the different rotation positions of said light intercepting means.

3. The optical inspecting apparatus according to claim 1, wherein said centering means controls said moving means so that the optical axis of said optical element coincides with said rotation axis.

4. The optical inspecting apparatus according to claim 3, wherein said determining means determines said deviation by comparing brightness distributions of said images detected at the different rotation positions of said light intercepting means.

5. The optical inspecting apparatus according to claim 1, wherein said centering means controls said moving means so that a center of an outline of said optical element coincides with said rotation axis.

6. The optical inspecting apparatus according to claim 1, wherein said centering means controls said moving means so that a gravity point of said optical element coincides with said rotation axis.

7. The optical inspecting apparatus according to claim 1, wherein said illuminating means comprises a light source and a diffuser plate located between said light source and said light intercepting means.

8. The optical inspecting apparatus according to claim 7, wherein said diffuser plate has a circular shape and said light intercepting means is a lighting intercepting plate having a semicircular shape.

9. The optical inspecting apparatus according to claim 8, wherein said light intercepting plate is attached to said diffuser plate so that said rotating means rotate said diffuser plate together with said light intercepting plate, and wherein said straight boundary line comprises a diameter of said diffuser plate.

10. The optical inspecting apparatus according to claim 1, wherein said detecting means comprises a photographing lens and an image detecting element having a plurality of pixels that are arranged in a two dimensional array, each said pixel of said plurality of pixels outputting brightness data of a point in the detected image.

11. The optical inspecting apparatus according to claim 10, wherein said optical element is optically conjugate with said image detecting element via said photographing lens.

12. The optical inspecting apparatus according to claim 11, wherein said moving means comprises an X-Y stage to move said optical element along x and y directions which are perpendicular to each other.

13. The optical inspecting apparatus according to claim 12, wherein said determining means comprises:

means for controlling said rotating means so that said light intercepting means is set at a 0 degree rotation position where said straight boundary line is parallel to the x direction, and 90 degrees, 180 degrees and 270 degrees rotation positions where the light intercepting means is rotated by 90 degrees, 180 degrees and 270 degrees respectively from said 0 degree rotation position;

means for accumulating the brightness data of pixels along a line parallel to the x direction and the y direction to find a total brightness in the x direction and a total brightness in the y direction;

first means for subtracting said total brightness in the y direction of the image captured at the 180 degrees rotation position from said total brightness in the y direction at the 0 degree rotation position to find a brightness difference in the y direction;

second means for subtracting said total brightness in the x direction of the image captured at the 270 degrees rotation position from said total brightness in the x direction at the 90 degrees rotation position to find a brightness difference in the x direction; and means for finding said deviations in the x and y directions based on said brightness differences in the x and y directions respectively.

14. The optical inspecting apparatus according to claim 13, further comprising a reference data memory in which the correspondence between said brightness difference and said deviation is defined.

15. The optical inspecting apparatus according to claim 14, wherein said finding means finds the deviation from said reference data memory that corresponds to the brightness difference from each of said first and second subtracting means.

16. The optical inspecting apparatus according to claim 13, wherein said centering means controls said X-Y stage to compensate for said deviations in the x and y directions found by said finding means.

17. The optical inspecting apparatus according to claim 13, wherein said controlling means controls said rotating means so that said light intercepting plate sequentially changes its position from the 0 degree, 180 degrees, 90 degrees and 270 degrees rotation positions, and said detecting means captures images at each of said rotation positions.

18. The optical inspecting apparatus according to claim 13, wherein said controlling means controls said rotating means so that said light intercepting plate sequentially changes its position from the 0 degree, 90 degrees, 180 degrees and 270 degrees rotation positions, and said detecting means captures images at each of said rotation positions.

19. The optical inspecting apparatus according to claim 18, wherein said accumulating means finds said total brightness at the 0 degree, 90 degrees, 180 degrees rotation positions while said light intercepting means is rotated.

20. The optical inspecting apparatus according to claim 12, wherein said determining means comprises:

means for controlling said rotating means so that said light, intercepting plate is set at 0 degree rotation position where said straight boundary line is parallel to the x direction, 90 degrees, 180 degrees and 270 degrees rotation positions where the light intercepting means is rotated by 90 degrees, 180 degrees and 270 degrees respectively from said 0 degree rotation position;

means for composing images detected by said detecting means at said four rotation positions;

means for extracting a mask image defining an essential portion of said optical element based on images composed by said composing means; and means for finding said deviations in the x and y directions of the center of said mask image from said rotation axis in an image field.

21. The optical inspecting apparatus according to claim 20, further comprising a reference data memory in which the coordinate of said rotation axis in the image field is defined.

22. An optical inspecting apparatus for detecting a defect of an optical element to be inspected, comprising:

a diffuser plate which is illuminated;

an interceptor that intercepts a portion of light diffused by said diffuser plate, said interceptor being located in contact with said diffuser plate and positioned so as to coincide with a focal point of an optical system including at least said optical element;

a rotator that rotates said interceptor about a rotation axis that intersects a boundary line between a light transmitting portion and a light blocking portion of said interceptor;

a detector that detects light transmitted through said optical system;

a calculator that calculates a brightness difference based on brightness distributions detected at different rotation positions of said interceptor; and a positioner that moves said optical element so that an optical axis of said optical element coincides with said rotation axis.

23. An optical inspecting apparatus for detecting a defect of an optical element to be inspected, said apparatus comprising:

a diffuser plate which is illuminated;

means for intercepting a portion of the light diffused by said diffuser plate, said light intercepting means being located in contact with said diffuser plate and positioned so as to coincide with a focal point of an optical system including at least said optical element;

means for rotating said light intercepting means about a rotation axis that intersects a boundary line between a light transmitting portion and a light blocking portion of said light intercepting means;

means for detecting light transmitted through said optical system;

means for finding a center of said optical element in an image of light detected by said detecting means;

means for finding said rotation axis in the image of light detected by said detecting means; and means for moving said optical element so that said center of said optical element coincides with said rotation axis in said image.

* * * * *

UNITED STATES PATENT AND TRADEMARK OFFICE
CERTIFICATE OF CORRECTION

PATENT NO. : 5,835,207
DATED : November 10, 1998
INVENTOR(S) : M. SUGIURA et al.

It is certified that error appears in the above-identified patent and that said Letters Patent is hereby corrected as shown below:

At column 16, line 11 (claim 2, line 2) of the printed patent, change "optical, element" to --- optical element---.

Signed and Sealed this

Fifteenth Day of June, 1999

Attest:

Attesting Officer

Q. TODD DICKINSON

Acting Commissioner of Patents and Trademarks